(12) United States Patent
Rosen et al.

(10) Patent No.: US 11,013,594 B2
(45) Date of Patent: May 25, 2021

(54) REALISTIC EYE MODELS TO DESIGN AND EVALUATE INTRAOCULAR LENSES FOR A LARGE FIELD OF VIEW

(71) Applicant: AMO GRONINGEN B.V., Groningen (NL)

(72) Inventors: Robert Rosen, Groningen (NL); Mihai State, Groningen (NL); Carmen Canovas Vidal, Groningen (NL); Aixa Alarcon Heredia, Groningen (NL); Marrie H. Van Der Mooren, Engelbert (NL)

(73) Assignee: AMO Groningen B.V., Groningen (NL)

( * ) Notice: Subject to any disclaimer, the term of this patent is extended or adjusted under 35 U.S.C. 154(b) by 0 days.

(21) Appl. No.: 15/792,574

(22) Filed: Oct. 24, 2017

(65) Prior Publication Data
US 2018/0153681 A1    Jun. 7, 2018

Related U.S. Application Data

(60) Provisional application No. 62/412,738, filed on Oct. 25, 2016.

(51) Int. Cl.
*A61F 2/16*   (2006.01)
*A61B 3/00*   (2006.01)

(52) U.S. Cl.
CPC ............. *A61F 2/16* (2013.01); *A61B 3/0025* (2013.01); *A61F 2240/001* (2013.01); *A61F 2240/002* (2013.01); *A61F 2240/007* (2013.01)

(58) Field of Classification Search
CPC ........... A61B 3/02; A61B 3/102; A61B 3/103; A61B 3/1035; A61B 3/107; A61B 3/117; A61B 3/16
See application file for complete search history.

(56) References Cited

U.S. PATENT DOCUMENTS 2,077,092 A    4/1937   Broder
3,305,294 A    2/1967   Alvarez
(Continued)

FOREIGN PATENT DOCUMENTS

DE    8107675 U1    7/1981
DE    3439551 A1    4/1986
(Continued)

OTHER PUBLICATIONS

Partial International Search Report for Application No. PCT/IB2017/001417, dated Feb. 9, 2018, 10 pages.
(Continued)

*Primary Examiner* — Darryl J Collins
*Assistant Examiner* — Journey F Sumlar
(74) *Attorney, Agent, or Firm* — Johnson & Johnson Surgical Vision, Inc.

(57) ABSTRACT

A system, method, and apparatus are provided for designing and evaluating intraocular lenses for a large field of view that generate a first eye model from data that includes constant and customized values, including customized values of a first intraocular lens. A simulated outcome is provided by the first intraocular lens in at least one modeled eye. A second eye model is generated wherein a second intraocular lens is substituted for the first intraocular lens. An outcome provided by the second intraocular lens is simulated in at least one modeled eye. Outcomes of the first and second intraocular lenses are compared.

12 Claims, 16 Drawing Sheets

(56) References Cited

U.S. PATENT DOCUMENTS

| | | |
|---|---|---|
| 3,367,734 A | 2/1968 | Karl et al. |
| 3,735,685 A | 5/1973 | Plummer |
| 4,010,496 A | 3/1977 | Neefe |
| 4,056,311 A | 11/1977 | Winthrop et al. |
| 4,077,071 A | 3/1978 | Freeman |
| 4,093,361 A | 6/1978 | Erickson et al. |
| 4,134,160 A | 1/1979 | Bayers |
| 4,162,122 A | 7/1979 | Cohen |
| 4,174,543 A | 11/1979 | Kelman |
| 4,210,391 A | 7/1980 | Cohen et al. |
| 4,249,272 A | 2/1981 | Poler |
| 4,254,509 A | 3/1981 | Tennant |
| 4,254,510 A | 3/1981 | Tennant |
| 4,316,293 A | 2/1982 | Bayers |
| 4,319,564 A | 3/1982 | Karickhoff |
| 4,338,005 A | 7/1982 | Cohen |
| 4,340,283 A | 7/1982 | Cohen et al. |
| 4,370,760 A | 2/1983 | Kelman |
| 4,377,873 A | 3/1983 | Reichert |
| 4,402,579 A | 9/1983 | Poler |
| 4,403,353 A | 9/1983 | Tennant |
| 4,404,694 A | 9/1983 | Kelman |
| 4,409,691 A | 10/1983 | Levy |
| 4,424,597 A | 1/1984 | Schlegel |
| 4,437,733 A | 3/1984 | Takahashi et al. |
| 4,446,581 A | 5/1984 | Blake |
| 4,480,340 A | 11/1984 | Shepard |
| 4,500,382 A | 2/1985 | Foster |
| 4,504,982 A | 3/1985 | Burk |
| 4,551,864 A | 11/1985 | Akhavi |
| 4,556,998 A | 12/1985 | Siepser |
| 4,560,383 A | 12/1985 | Leiske |
| 4,605,409 A | 8/1986 | Kelman |
| 4,605,411 A | 8/1986 | Fedorov et al. |
| 4,629,460 A | 12/1986 | Dyer |
| 4,629,462 A | 12/1986 | Feaster |
| 4,637,697 A | 1/1987 | Freeman |
| 4,642,112 A | 2/1987 | Freeman |
| 4,655,565 A | 4/1987 | Freeman |
| 4,665,913 A | 5/1987 | L'Esperance, Jr. |
| 4,669,466 A | 6/1987 | L'Esperance |
| 4,673,406 A | 6/1987 | Schlegel |
| 4,676,791 A | 6/1987 | Lemaster et al. |
| 4,676,792 A | 6/1987 | Praeger |
| 4,681,102 A | 7/1987 | Bartell |
| 4,687,484 A | 8/1987 | Kaplan |
| 4,687,485 A | 8/1987 | Lim et al. |
| RE32,525 E | 10/1987 | Pannu |
| 4,725,277 A | 2/1988 | Bissonette |
| 4,732,148 A | 3/1988 | L'Esperance, Jr. |
| 4,734,095 A | 3/1988 | Siepser |
| 4,764,930 A | 8/1988 | Bille et al. |
| 4,770,172 A | 9/1988 | L'Esperance, Jr. |
| 4,773,414 A | 9/1988 | L'Esperance, Jr. |
| 4,778,462 A | 10/1988 | Grendahl |
| 4,781,717 A | 11/1988 | Grendahl |
| 4,787,903 A | 11/1988 | Grendahl |
| 4,787,904 A | 11/1988 | Severin et al. |
| 4,795,462 A | 1/1989 | Grendahl |
| 4,798,608 A | 1/1989 | Grendahl |
| 4,798,609 A | 1/1989 | Grendahl |
| 4,828,558 A | 5/1989 | Kelman |
| 4,834,748 A | 5/1989 | McDonald |
| 4,863,261 A | 9/1989 | Flammer |
| 4,863,539 A | 9/1989 | Lee et al. |
| 4,898,461 A | 2/1990 | Portney |
| 4,932,970 A | 6/1990 | Portney |
| 4,995,714 A | 2/1991 | Cohen |
| 4,995,715 A | 2/1991 | Cohen |
| 4,997,442 A | 3/1991 | Barrett |
| 5,016,977 A | 5/1991 | Baude et al. |
| 5,019,097 A | 5/1991 | Knight et al. |
| 5,042,938 A | 8/1991 | Shimozono |
| 5,047,052 A | 9/1991 | Dubroff |
| 5,054,905 A | 10/1991 | Cohen |
| 5,056,908 A | 10/1991 | Cohen |
| 5,066,301 A | 11/1991 | Wiley |
| 5,071,432 A | 12/1991 | Baikoff |
| 5,078,742 A | 1/1992 | Dahan |
| 5,089,023 A | 2/1992 | Swanson |
| 5,096,285 A | 3/1992 | Silberman |
| 5,108,388 A | 4/1992 | Trokel et al. |
| 5,114,220 A | 5/1992 | Baude et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,133,749 A | 7/1992 | Nordan |
| 5,144,483 A | 9/1992 | Cohen |
| 5,147,395 A | 9/1992 | Willis |
| 5,147,397 A | 9/1992 | Christ et al. |
| 5,163,934 A | 11/1992 | Munnerlyn |
| 5,173,723 A | 12/1992 | Volk et al. |
| 5,184,405 A | 2/1993 | Cress |
| 5,197,981 A | 3/1993 | Southard |
| 5,201,763 A | 4/1993 | Brady et al. |
| 5,203,790 A | 4/1993 | McDonald |
| 5,207,668 A | 5/1993 | L'Esperance, Jr. |
| 5,217,491 A | 6/1993 | Vanderbilt |
| 5,219,343 A | 6/1993 | L'Esperance, Jr. |
| 5,225,858 A | 7/1993 | Portney |
| 5,229,797 A | 7/1993 | Futhey et al. |
| 5,258,025 A | 11/1993 | Fedorov et al. |
| 5,278,592 A | 1/1994 | Marie et al. |
| 5,379,110 A | 1/1995 | Matsui et al. |
| 5,408,281 A | 4/1995 | Zhang |
| 5,433,745 A | 7/1995 | Graham et al. |
| 5,476,513 A | 12/1995 | Brady et al. |
| 5,479,220 A | 12/1995 | Komatsu et al. |
| 5,567,365 A | 10/1996 | Weinschenk, III et al. |
| 5,571,177 A | 11/1996 | Deacon et al. |
| 5,620,720 A | 4/1997 | Glick et al. |
| 5,628,796 A | 5/1997 | Suzuki |
| 5,646,791 A | 7/1997 | Glockler |
| 5,652,638 A | 7/1997 | Roffman et al. |
| 5,652,640 A | 7/1997 | Schneider et al. |
| 5,691,800 A | 11/1997 | Iki et al. |
| 5,699,142 A | 12/1997 | Lee et al. |
| 5,716,403 A | 2/1998 | Tran et al. |
| 5,748,282 A | 5/1998 | Freeman |
| 5,760,871 A | 6/1998 | Kosoburd et al. |
| 5,796,462 A | 8/1998 | Roffman et al. |
| 5,801,807 A | 9/1998 | Satake et al. |
| 5,928,282 A | 7/1999 | Nigam |
| 5,968,094 A | 10/1999 | Werblin et al. |
| 5,993,438 A | 11/1999 | Juhasz et al. |
| 6,015,435 A | 1/2000 | Valunin et al. |
| 6,051,024 A | 4/2000 | Cumming |
| 6,126,283 A | 10/2000 | Wen et al. |
| 6,126,286 A | 10/2000 | Portney |
| 6,129,759 A | 10/2000 | Chambers |
| 6,142,625 A | 11/2000 | Sawano et al. |
| 6,179,870 B1 | 1/2001 | Sourdille et al. |
| 6,210,005 B1 | 4/2001 | Portney |
| 6,235,055 B1 | 5/2001 | Chu |
| 6,241,356 B1 | 6/2001 | Von Wallfeld et al. |
| 6,261,321 B1 | 7/2001 | Kellan |
| 6,319,282 B1 | 11/2001 | Nishi |
| 6,338,559 B1 | 1/2002 | Williams et al. |
| 6,419,697 B1 | 7/2002 | Kelman |
| 6,457,826 B1 | 10/2002 | Lett |
| 6,460,997 B1 | 10/2002 | Frey et al. |
| 6,464,355 B1 | 10/2002 | Gil |
| 6,474,814 B1 | 11/2002 | Griffin |
| 6,488,708 B2 | 12/2002 | Sarfarazi |
| 6,491,721 B2 | 12/2002 | Freeman et al. |
| 6,497,483 B2 | 12/2002 | Frey et al. |
| 6,527,389 B2 | 3/2003 | Portney |
| 6,533,416 B1 | 3/2003 | Fermigier et al. |
| 6,536,899 B1 | 3/2003 | Fiala |
| 6,537,317 B1 | 3/2003 | Steinert et al. |
| 6,547,822 B1 | 4/2003 | Lang |
| 6,550,917 B1 | 4/2003 | Neal et al. |
| 6,554,859 B1 | 4/2003 | Lang et al. |

(56) References Cited

U.S. PATENT DOCUMENTS

| | | |
|---|---|---|
| 6,557,992 B1 | 5/2003 | Dwyer et al. |
| 6,575,572 B2 | 6/2003 | Lai et al. |
| 6,598,606 B2 | 7/2003 | Terwee et al. |
| 6,609,793 B2 | 8/2003 | Norrby et al. |
| 6,705,729 B2 | 3/2004 | Piers et al. |
| 6,786,603 B2 | 9/2004 | Altmann |
| 6,802,605 B2 | 10/2004 | Cox et al. |
| 6,808,262 B2 | 10/2004 | Chapoy et al. |
| 6,817,714 B2 | 11/2004 | Altmann |
| 6,830,332 B2 | 12/2004 | Piers et al. |
| 6,846,326 B2 | 1/2005 | Zadno-Azizi et al. |
| 6,851,803 B2 | 2/2005 | Wooley et al. |
| 6,899,425 B2 | 5/2005 | Roffman et al. |
| 6,923,539 B2 | 8/2005 | Simpson et al. |
| 6,923,540 B2 | 8/2005 | Ye et al. |
| 6,986,578 B2 | 1/2006 | Jones |
| 7,036,931 B2 | 5/2006 | Lindacher et al. |
| 7,048,760 B2 | 5/2006 | Cumming |
| 7,061,693 B2 | 6/2006 | Zalevsky |
| 7,073,906 B1 | 7/2006 | Portney |
| 7,137,702 B2 | 11/2006 | Piers et al. |
| 7,156,516 B2 | 1/2007 | Morris et al. |
| 7,188,949 B2 | 3/2007 | Bandhauer et al. |
| 7,281,797 B2 | 10/2007 | Yamaguchi et al. |
| 7,287,852 B2 | 10/2007 | Fiala |
| 7,293,873 B2 | 11/2007 | Dai et al. |
| 7,296,893 B2 | 11/2007 | Dai |
| 7,339,539 B2 | 3/2008 | Joannopoulos et al. |
| 7,350,916 B2 | 4/2008 | Hong et al. |
| 7,365,917 B2 | 4/2008 | Zalevsky |
| 7,377,640 B2 | 5/2008 | Piers et al. |
| 7,425,068 B2 | 9/2008 | Koest |
| 7,441,894 B2 | 10/2008 | Zhang et al. |
| 7,455,404 B2 | 11/2008 | Bandhauer et al. |
| 7,455,407 B2 | 11/2008 | Neal et al. |
| 7,475,986 B2 | 1/2009 | Dai et al. |
| 7,547,102 B2 | 6/2009 | Dai |
| 7,615,073 B2 | 11/2009 | Deacon et al. |
| 7,616,330 B2 | 11/2009 | Neal et al. |
| 7,659,971 B2 | 2/2010 | Warden et al. |
| 7,726,813 B2 | 6/2010 | Dai |
| 7,784,946 B2 | 8/2010 | Leblanc |
| 7,794,497 B2 | 9/2010 | Brady et al. |
| 7,857,451 B2 | 12/2010 | Thibos et al. |
| 7,871,162 B2 | 1/2011 | Weeber |
| 7,911,211 B2 | 3/2011 | Crain et al. |
| 7,931,371 B2 | 4/2011 | Dai |
| 7,931,374 B2 | 4/2011 | Dai et al. |
| 7,938,538 B2 | 5/2011 | Lu et al. |
| 7,944,553 B1 | 5/2011 | Simpson et al. |
| 7,969,585 B2 | 6/2011 | Neal et al. |
| 8,123,357 B2 | 2/2012 | Dai et al. |
| 8,382,281 B2 | 2/2013 | Weeber |
| 8,480,228 B2 | 7/2013 | Weeber |
| 8,596,787 B2 | 12/2013 | Dai |
| 8,657,445 B2 | 2/2014 | Olsen |
| 8,696,119 B2 | 4/2014 | Van Der Mooren et al. |
| 8,740,382 B1 | 6/2014 | Liu et al. |
| 8,746,882 B2 | 6/2014 | Vidal et al. |
| 8,764,822 B2 | 7/2014 | Harris et al. |
| 8,862,447 B2 | 10/2014 | Weeber |
| 9,211,061 B2 | 12/2015 | Kasthurirangan et al. |
| 9,241,627 B2 | 1/2016 | Steinmueller |
| 9,393,108 B2 | 7/2016 | Canovas Vidal et al. |
| 9,491,431 B2 | 11/2016 | Zhou |
| 9,700,201 B2 | 7/2017 | Bex et al. |
| 2001/0051825 A1 | 12/2001 | Peterson |
| 2002/0118337 A1 | 8/2002 | Perrott et al. |
| 2002/0173846 A1 | 11/2002 | Blake et al. |
| 2002/0196408 A1 | 12/2002 | Bhalakia et al. |
| 2002/0196412 A1 | 12/2002 | Abitbol |
| 2003/0033013 A1 | 2/2003 | Callahan et al. |
| 2003/0053025 A1 | 3/2003 | Turner et al. |
| 2003/0076478 A1 | 4/2003 | Cox |
| 2003/0163122 A1 | 8/2003 | Sumiya |
| 2003/0171808 A1 | 9/2003 | Phillips |
| 2003/0189690 A1 | 10/2003 | Mihashi et al. |
| 2004/0021824 A1 | 2/2004 | Ye et al. |
| 2004/0021825 A1 | 2/2004 | Richardson |
| 2004/0054358 A1 | 3/2004 | Cox |
| 2004/0057010 A1 | 3/2004 | Altmann |
| 2004/0068317 A1 | 4/2004 | Knight |
| 2004/0085515 A1 | 5/2004 | Roffman et al. |
| 2004/0106992 A1 | 6/2004 | Lang et al. |
| 2004/0111153 A1 | 6/2004 | Woods et al. |
| 2004/0150789 A1 | 8/2004 | Jones |
| 2004/0156014 A1 | 8/2004 | Piers et al. |
| 2004/0167622 A1 | 8/2004 | Sunalp et al. |
| 2004/0183997 A1 | 9/2004 | Suzuki |
| 2004/0230299 A1 | 11/2004 | Simpson et al. |
| 2004/0260275 A1 | 12/2004 | Liang et al. |
| 2005/0024647 A1 | 2/2005 | Montgomery |
| 2005/0096226 A1 | 5/2005 | Stock et al. |
| 2005/0122474 A1 | 6/2005 | Koretz |
| 2005/0125056 A1 | 6/2005 | Deacon et al. |
| 2005/0128432 A1 | 6/2005 | Altmann |
| 2005/0195364 A1 | 9/2005 | Dai |
| 2005/0203619 A1 | 9/2005 | Altmann |
| 2005/0251254 A1 | 11/2005 | Brady et al. |
| 2005/0267575 A1 | 12/2005 | Nguyen et al. |
| 2006/0009816 A1 | 1/2006 | Fang et al. |
| 2006/0030938 A1 | 2/2006 | Altmann |
| 2006/0034003 A1 | 2/2006 | Zalevsky |
| 2006/0055877 A1 | 3/2006 | Yanari |
| 2006/0055883 A1 | 3/2006 | Morris et al. |
| 2006/0066808 A1 | 3/2006 | Blum et al. |
| 2006/0068453 A1 | 3/2006 | Altieri |
| 2006/0098162 A1 | 5/2006 | Bandhauer et al. |
| 2006/0098163 A1 | 5/2006 | Bandhauer et al. |
| 2006/0109421 A1 | 5/2006 | Ye et al. |
| 2006/0116763 A1 | 6/2006 | Simpson |
| 2006/0116764 A1 | 6/2006 | Simpson |
| 2006/0116765 A1 | 6/2006 | Blake et al. |
| 2006/0176572 A1 | 8/2006 | Fiala |
| 2006/0203198 A1 | 9/2006 | Liang |
| 2006/0238702 A1 | 10/2006 | Glick et al. |
| 2006/0244904 A1 | 11/2006 | Hong et al. |
| 2006/0244906 A1 | 11/2006 | Piers et al. |
| 2006/0244916 A1 | 11/2006 | Guillon |
| 2006/0274268 A1 | 12/2006 | Andino et al. |
| 2006/0279699 A1 | 12/2006 | Liang |
| 2006/0279700 A1 | 12/2006 | Liang |
| 2007/0052920 A1 | 3/2007 | Stewart et al. |
| 2007/0052927 A1 | 3/2007 | Noda et al. |
| 2007/0129803 A1 | 6/2007 | Cumming et al. |
| 2007/0171362 A1 | 7/2007 | Simpson et al. |
| 2007/0182924 A1 | 8/2007 | Hong et al. |
| 2007/0195265 A1 | 8/2007 | Dreher et al. |
| 2007/0211214 A1 | 9/2007 | Dai |
| 2007/0268453 A1 | 11/2007 | Hong et al. |
| 2007/0285617 A1 | 12/2007 | Mills et al. |
| 2008/0018910 A1 | 1/2008 | Neal et al. |
| 2008/0030677 A1 | 2/2008 | Simpson |
| 2008/0033546 A1 | 2/2008 | Liang |
| 2008/0161913 A1 | 7/2008 | Brady et al. |
| 2008/0161914 A1 | 7/2008 | Brady et al. |
| 2008/0198331 A1 | 8/2008 | Azar et al. |
| 2008/0231809 A1 | 9/2008 | Haigis |
| 2008/0269642 A1 | 10/2008 | Deacon et al. |
| 2008/0273169 A1 | 11/2008 | Blum et al. |
| 2008/0291393 A1 | 11/2008 | Menezes |
| 2009/0000628 A1 | 1/2009 | Somani et al. |
| 2009/0012609 A1 | 1/2009 | Geraghty et al. |
| 2009/0036980 A1 | 2/2009 | Norrby et al. |
| 2009/0062911 A1 | 3/2009 | Bogaert |
| 2009/0164008 A1 | 6/2009 | Hong et al. |
| 2009/0168019 A1 | 7/2009 | Tuan |
| 2009/0187242 A1 | 7/2009 | Weeber et al. |
| 2009/0210054 A1 | 8/2009 | Weeber et al. |
| 2009/0231546 A1 | 9/2009 | Dai |
| 2009/0234448 A1 | 9/2009 | Weeber et al. |
| 2009/0268155 A1 | 10/2009 | Weeber |
| 2009/0268158 A1 | 10/2009 | Weeber |
| 2009/0275929 A1 | 11/2009 | Zickler |

(56) References Cited

U.S. PATENT DOCUMENTS

| | | |
|---|---|---|
| 2009/0279048 A1 | 11/2009 | Hong et al. |
| 2009/0281552 A1 | 11/2009 | Hiramatsu et al. |
| 2009/0292354 A1 | 11/2009 | Gontijo et al. |
| 2009/0295295 A1 | 12/2009 | Shannon et al. |
| 2009/0303465 A1 | 12/2009 | Clements et al. |
| 2009/0323020 A1 | 12/2009 | Zhao et al. |
| 2010/0016961 A1 | 1/2010 | Hong et al. |
| 2010/0016965 A1 | 1/2010 | Hong et al. |
| 2010/0082017 A1 | 4/2010 | Zickler et al. |
| 2010/0097569 A1 | 4/2010 | Weeber et al. |
| 2010/0130888 A1 | 5/2010 | Deacon et al. |
| 2010/0161048 A1 | 6/2010 | Schaper, Jr. |
| 2010/0179793 A1 | 7/2010 | Chernyak et al. |
| 2010/0220185 A1 | 9/2010 | Vertoprakhov et al. |
| 2010/0234833 A1 | 9/2010 | Dai |
| 2010/0315589 A1 | 12/2010 | Portney |
| 2011/0080562 A1 | 4/2011 | Iizuka et al. |
| 2011/0149236 A1 | 6/2011 | Weeber |
| 2011/0166652 A1 | 7/2011 | Bogaert et al. |
| 2011/0205486 A1 | 8/2011 | Zhao |
| 2011/0211163 A1 | 9/2011 | Meuse et al. |
| 2011/0270596 A1* | 11/2011 | Weeber ................ A61F 2/16 703/11 |
| 2012/0140166 A1 | 6/2012 | Zhao |
| 2012/0238904 A1 | 9/2012 | Manns et al. |
| 2012/0249955 A1 | 10/2012 | Sarver et al. |
| 2012/0310337 A1 | 12/2012 | Hacker et al. |
| 2013/0050637 A1 | 2/2013 | Roffman et al. |
| 2013/0226294 A1 | 8/2013 | Van Der Mooren et al. |
| 2013/0307965 A1 | 11/2013 | Widman et al. |
| 2013/0314669 A1 | 11/2013 | Levin et al. |
| 2013/0345807 A1 | 12/2013 | Olsen et al. |
| 2014/0016088 A1 | 1/2014 | De Rossi et al. |
| 2014/0135919 A1 | 5/2014 | Gontijo et al. |
| 2014/0160436 A1 | 6/2014 | Kasthurirangan et al. |
| 2014/0176904 A1 | 6/2014 | Lai |
| 2014/0268042 A1 | 9/2014 | Bor et al. |
| 2014/0293426 A1 | 10/2014 | Dobschal |
| 2014/0320805 A1 | 10/2014 | Wilzbach et al. |
| 2015/0062529 A1 | 3/2015 | Kasthurirangan et al. |
| 2015/0138350 A1 | 5/2015 | Videcoq |
| 2015/0250583 A1 | 9/2015 | Rosen et al. |
| 2015/0320547 A1* | 11/2015 | Rosen ................ A61F 2/164 623/6.23 |
| 2015/0359625 A1 | 12/2015 | Argal et al. |
| 2015/0362746 A1 | 12/2015 | Skudder et al. |
| 2015/0379348 A1 | 12/2015 | Whritenor et al. |
| 2016/0157997 A1 | 6/2016 | Gerlach et al. |
| 2016/0299355 A1 | 10/2016 | Biemold et al. |
| 2016/0335474 A1* | 11/2016 | Santos-Villalobos ........................ G06K 9/0061 |
| 2017/0189233 A1* | 7/2017 | Dewey ................ A61F 9/00827 |

FOREIGN PATENT DOCUMENTS

| | | |
|---|---|---|
| DE | 102005022683 A1 | 11/2006 |
| EP | 226400 A2 | 6/1987 |
| EP | 227357 A2 | 7/1987 |
| EP | 0343067 A1 | 11/1989 |
| EP | 0457553 A2 | 11/1991 |
| EP | 681198 A1 | 11/1995 |
| EP | 0538126 B1 | 9/1996 |
| EP | 0810427 A1 | 12/1997 |
| EP | 0926531 A1 | 6/1999 |
| EP | 949529 A2 | 10/1999 |
| EP | 957331 A2 | 11/1999 |
| EP | 1424049 A1 | 6/2004 |
| EP | 1857077 A1 | 11/2007 |
| EP | 1310267 B1 | 1/2008 |
| EP | 1424049 B1 | 6/2009 |
| EP | 2631891 A1 | 8/2013 |
| EP | 3059575 A1 | 8/2016 |
| FR | 2745711 A1 | 9/1997 |
| GB | 2433782 A | 7/2007 |
| GB | 2488802 A | 9/2012 |
| WO | 8603961 A1 | 7/1986 |
| WO | 9222264 A1 | 12/1992 |
| WO | 9303409 A1 | 2/1993 |
| WO | 9507487 A1 | 3/1995 |
| WO | 9856315 A1 | 12/1998 |
| WO | 9905499 A1 | 2/1999 |
| WO | 0019906 A1 | 4/2000 |
| WO | 0111418 A1 | 2/2001 |
| WO | 0135868 A1 | 5/2001 |
| WO | 0154569 A1 | 8/2001 |
| WO | 0163344 A1 | 8/2001 |
| WO | 0182839 A1 | 11/2001 |
| WO | 0185016 A2 | 11/2001 |
| WO | 0189424 A1 | 11/2001 |
| WO | 0221194 A2 | 3/2002 |
| WO | 02074210 A2 | 9/2002 |
| WO | 03009053 A1 | 1/2003 |
| WO | 04028356 A1 | 4/2004 |
| WO | 2004034129 A1 | 4/2004 |
| WO | 2004053568 A1 | 6/2004 |
| WO | 2004079637 A1 | 9/2004 |
| WO | 2004090611 A2 | 10/2004 |
| WO | 2004096014 A2 | 11/2004 |
| WO | 05019906 A1 | 3/2005 |
| WO | 2005079546 A2 | 9/2005 |
| WO | 06025726 A1 | 3/2006 |
| WO | 2006032263 A2 | 3/2006 |
| WO | 2006047698 A1 | 5/2006 |
| WO | 06060477 A2 | 6/2006 |
| WO | 2006060480 A2 | 6/2006 |
| WO | 2007067872 A2 | 6/2007 |
| WO | 2007092948 A1 | 8/2007 |
| WO | 2007133384 A2 | 11/2007 |
| WO | 2007142981 A2 | 12/2007 |
| WO | 2008045847 A2 | 4/2008 |
| WO | 2008083283 A2 | 7/2008 |
| WO | 2009020963 A1 | 2/2009 |
| WO | 2009029515 A1 | 3/2009 |
| WO | 2009076670 A1 | 6/2009 |
| WO | 2009105567 A1 | 8/2009 |
| WO | 2009137491 A1 | 11/2009 |
| WO | 2010009254 A1 | 1/2010 |
| WO | 2010009257 A1 | 1/2010 |
| WO | 2010028654 A1 | 3/2010 |
| WO | 2012052585 A1 | 4/2012 |
| WO | 2012074742 A1 | 6/2012 |
| WO | 2012083143 A1 | 6/2012 |
| WO | 2012085917 A1 | 6/2012 |
| WO | 2012154597 A1 | 11/2012 |
| WO | 2012166797 A1 | 12/2012 |
| WO | 2015022215 A1 | 2/2015 |
| WO | 2016032397 A1 | 3/2016 |
| WO | 2016087914 A1 | 6/2016 |
| WO | 2016123167 A1 | 8/2016 |

OTHER PUBLICATIONS

Einighammer H.J., "The Individual Virtual Eye", Dissertation, 2008, 157 pages.

Abelman H., et al. "Tolerance and Nature of Residual Refraction in Symmetric Power Space as Principal Lens Powers and Meridians Change," Computational and Mathematical Methods in Medicine, Article ID 492383, 2014, vol. 2014, pp. 1-12.

Alfonso J.F., et al., "Prospective Study of the Acri.LISA Bifocal Intraocular Lens," Journal of Cataract Refractive Surgery, Nov. 2007, vol. 33 (11), pp. 1930-1935.

Alio J.L., et al., "Phakic Anterior Chamber Lenses for the Correction of Myopia: A 7-Year Cumulative Analysis of Complications in 263 Cases," Ophthalmology, Mar. 1999, vol. 106 (3), pp. 458-466.

Apple D.J., et al., "Anterior Chamber Lenses Part 1: Complications and Pathology and a Review of Designs," Journal of Cataract Refractive Surgery, Mar. 1987, vol. 13 (2), pp. 157-174.

Apple D.J., et al., Eds., "Intraocular Lenses: Evolution, Designs, Complications and Pathology," in: New Concepts in Intraocular Lens Implantation, Williams & Wilkins publisher, Jan. 1989, vol. 22 (36), pp. 205-221.

(56) References Cited

OTHER PUBLICATIONS

Apple D.J., et al., Eds., "Intraocular Lenses: Evolution, Designs, Complications and Pathology," in: New Concepts in Intraocular Lens Implantation, Williams & Wilkins publisher, Jan. 1989, vol. 36 (1), pp. 21-36.
Baikoff G., et al., "Angle-fixated Anterior Chamber Phakic Intraocular Lens for Myopia 7 to -19 Diopters," Journal of Refractive Surgery, May-Jun. 1998, vol. 14 (3), pp. 282-292.
Baumeister M., et al., "Tilt and Decentration of Spherical and Aspheric Intraocular Lenses: Effect on Higher-Order Aberrations," Journal of Cataract & Refractive Surgery, 2009, vol. 35 (6), pp. 1006-1012.
Brainard D.H., The Psychophysics Toolbox, Spatial Vision, vol. 10, pp. 433-436.
Brown W.L., "Revisions to Tolerances in Cylinder Axis and in Progressive Addition Lens Power in ANSI Z80.1-2005," Optometry, 2006, vol. 77 (7), pp. 343-349.
Canovas C., et al., "Customized Eye Models for Determining Optimized Intraocular Lenses Power," Biomedical Optics Express, Jun. 1, 2011, vol. 2 (6), pp. 1649-1662.
Canovas C., et al., "Hybrid Adaptive-Optics Visual Simulator," Optical Letters, Jan. 15, 2010, vol. 35 (2), pp. 196-198.
Cheng X., et al., "Predicting Subjective Judgment of Best Focus with Objective Image Quality Metrics," Journal of Vision, Apr. 2004, vol. 4 (4), pp. 310-321.
CILCO Advertisement Brochure, Oct. 1982, 3 pages.
Cohen A.L., "Practical Design of a Bifocal Hologram Contact Lens or Intraocular Lens," Applied Optics, Jul. 1, 1992, vol. 31 (19), pp. 3750-3754.
De Almeida M.S., et al., "Different Schematic Eyes and their Accuracy to the in Vivo Eye: A Quantitative Comparison Study," Brazilian Journal of Physics, Jun. 2007, vol. 37 (2A), 10 pages.
Diffractive Lenses for Extended Depth of Focus and Presbyopic Correction, Presentation from Wavefront Congress held on Feb. 15, 2008, Rochester, New York.
Doskolovich L.L., et al., "Special Diffractive Lenses," Lens and Optical Systems Design, Apr. 1992, vol. 1780, pp. 393-402.
Gobbi P.G., et al., "Far and Near Visual Acuity with Multifocal Intraocular Lenses in an Optomechanical Eye Model with Imaging Capability," Journal of Cataract and Refractive Surgery, 2007, vol. 33 (6), pp. 1082-1094.
Gobbi P.G., et al., "Optomechanical Eye Model with Imaging Capabilities for Objective Evaluation of Intraocular Lenses," Journal of Cataract and Refractive Surgery, 2006, vol. 32 (4), pp. 643-651.
Hill W., et al., "Monte Carlo Simulation of Expected Outcomes with the Acrysof Toric Intraocular Lens," BMC Ophthalmology, Oct. 2008, vol. 8, pp. 22.
Kim J.H., et al., "The Analysis of Predicted Capsular Bag Diameter using Modified Model of Capsule Measuring Ring in Asians," Clinical and Experimental Ophthalmology, Apr. 2008, vol. 36 (3), pp. 238-244.
Kim M.J., et al., "Objective Evaluation of Through-Focus Optical Performance of Presbyopia-Correcting Intraocular Lenses Using an Optical Bench System," Journal of Cataract and Refractive Surgery, 2011, vol. 37 (7), pp. 1305-1312.
Klein S.A., "Optimal Corneal Ablation for Eyes with Arbitrary Hartmann-Shack Aberrations," Journal of the Optical Society of America A, 1998, vol. 15 (9), pp. 2580-2588.
Liang J., et al, "Objective Measurement of Wave Aberrations of the Human Eye With the Use of a Hartmann-Shack Wave-Front Sensor," Journal of the Optical Society of America, 1994, vol. 11 (7), pp. 1949-1957.
Liou H.L., et al., "Anatomically Accurate, Finite Model Eye for Optical Modeling," Journal of Optical Society of America, Aug. 1997, vol. 14 (8), pp. 1684-1695.
Liou H.L., et al., "The Prediction of Spherical Aberration with Schematic Eyes," Ophthalmic and Physiological Optics, Jan. 1996, vol. 16 (4), pp. 348-354.

Marinho A., "Results are Encouraging for Phakic IOLs, but More Work is needed," Refractive Surgery, Feb. 2000, p. 12, 15.
Marsack J.D., et al., "Metrics of Optical Quality Derived from Wave Aberrations Predict Visual Performance," Journal of Vision, Apr. 2004, vol. 4 (4), pp. 322-328.
Menapace R., "The Capsular Tension Rings," Journal of Cataract & Refractive Surgery, Dec. 10, 2008, Chap. 3, pp. 27-44.
Mencucci R., et al., "Clinical outcomes and rotational stability of a 4-haptic toric intraocular lens in myopic eyes," Journal of Cataract & Refractive Surgery, Sep. 2014, vol. 40 (9), pp. 1479-1487.
Monsoriu J.A., et al., "Devil's Lenses," Optics Express, Oct. 17, 2007, vol. 15 (21), pp. 13858-13864.
Navarro R., et al., "Accommodation-Dependent Model of the Human Eye with Aspherics," Journal of the Optical Society of America, Aug. 1985, vol. 2 (8), pp. 1273-1281.
Nio Y.K., et al., "Effect of Intraocular Lens Implantation on Visual Acuity, Contrast Sensitivity, and Depth of Focus," Journal of Cataract and Refractive Surgery, Nov. 2003, vol. 29 (11), pp. 2073-2081.
Norrby S., et al., "Model Eyes for Evaluation of Intraocular Lenses," Applied Optics, Sep. 7, 2007, vol. 46 (26), pp. 6595-6605.
Olsen T., "Simple Method to Calculate the Surgically Induced Refractive Change," Journal of Cataract & Refractive Surgery, Mar. 1993, vol. 19 (2), pp. 319-320.
Peli E., et al., "Appearance of Images Through a Multifocal Intraocular Lens," Journal of the Optical Society of America, 2001, vol. 18 (2), pp. 302-309.
Piers P.A., et al., "Eye Models for the Prediction of Contrast Vision in Patients with New Intraocular Lens Designs," Optics Letters, Apr. 1, 2004, vol. 29 (7), pp. 733-735.
Piers P.A., et al., "Theoretical Comparison of Aberration-Correcting Customized and Aspheric Intraocular Lenses," Journal of Refractive Surgery, Apr. 2007, vol. 23 (4), pp. 374-384.
Praeger D.L., "Praeger Technique for the Insertion of the Copeland Radial IOL Posterior Chamber Placement," Copeland Lens, 1982, 7 pages.
Siedlecki D., et al., "Radial Gradient index Intraocular Lens: a Theoretical Model," Journal of Modern Optics, Feb. 20-Mar. 10, 2008, vol. 55 (4-5), pp. 639-647.
Strenn K., et al., "Capsular bag Shrinkage after Implantation of an Open-Loop Silicone Lens and a Poly(methyl methacrylate) Capsule Tension Ring," Journal of Cataract and Refractive Surgery, Dec. 1997, vol. 23 (10), pp. 1543-1547.
Tehrani M., et al., "Capsule Measuring Ring to Predict Capsular Bag Diameter and Follow its Course after Foldable Intraocular Lens Implantation," Journal of Cataract Refractive Surgery, Nov. 2003, vol. 29 (11), pp. 2127-2134.
Terwee T., et al., "Visualization of the Retinal Image in an Eye Model With Spherical and Aspheric, Diffractive, and Refractive Multifocal Intraocular Lenses," Journal of Refractive Surgery, Mar. 2008, vol. 24 (3), pp. 223-232.
Van Den Berg T.J., "Analysis of Intraocular Straylight, Especially in Relation to Age," Optometry and Vision Science, Feb. 1995, vol. 72 (2), pp. 52-59.
Van Meeteren A., "Calculations on the Optical Modulation Transfer Function of the Human Eye for White Light," Optica Acta, May 1974, vol. 21 (5), pp. 395-412.
Vass C., et al., "Prediction of Pseudophakic Capsular bag Diameter based on Biometric Variables," Journal of Cataract and Refractive Surgery, Oct. 1999, vol. 25 (10), pp. 1376-1381.
Villegas E.A., et al., "Correlation between Optical and Psychophy, Sical Parameters as a Function of Defocus," Optometry and Vision Science, Jan. 1, 2002, vol. 79 (1), pp. 60-67.
Abrahamsson M., et al., "Impairment of Contrast Sensitivity Function (CSF) as a Measure of Disability Glare," Investigative Ophthalmology & Visual Science, Jul. 1986, vol. 27 (7), pp. 1131-1136.
Aslam, T.M., et al., "Development of a Forced Choice Photographic Questionnaire for Photic Phenomena and Its Testing—Repeatability, Reliability and Validity," Ophthalmologica, Nov.-Dec. 2004, vol. 218 (6), pp. 402-410.
Beer J.M., et al., "Lasers' Spectral and Temporal Profile Can Affect Visual Glare Disability," Aviation, Space, and Environmental Medicine, Dec. 2012, vol. 83 (12), pp. 1135-1144.

(56) References Cited

OTHER PUBLICATIONS

Calatayud A., et al., "Imaging Quality of Multifocal Intraocular Lenses: Automated Assessment Setup," Ophthalmic and Physiological Optics, Jul. 2013, vol. 33 (4), pp. 420-426.

Fernandez E.J., et al., "Adaptive Optics Visual Simulator," Journal of Refractive Surgery, 2002, vol. 18 (5), pp. 5634-S638.

Guirao A., et al., "Corneal Wave Aberration from Videokeratography: Accuracy and Limitations of the Procedure," Journal of the Optical Society of America, 2000, vol. 17 (6), pp. 955-965.

Jaeken B., et al., "Peripheral Aberrations in the Human Eye for Different Wavelengths: Off-Axis Chromatic Aberration," Journal of the Optical Society of America A, Sep. 2011, vol. 28 (9), pp. 1871-1879.

Javitt J.C., et al., "Validity and Reliability of the Cataract TyPE Spec: an Instrument for Measuring Outcomes of Cataract Extraction," American Journal of Ophthalmology, Aug. 2003, vol. 136 (2), pp. 285-290.

Jendritza B.B., et al., "Wavefront-Guided Excimer Laser Vision Correction after Multifocal IOL Implantation," Journal of Refractive Surgery, Mar. 2008, vol. 24 (3), pp. 274-279.

Johnson C.A., "Psychophysical Factors that Have Been Applied to Clinical Perimetry," Vision Research, Sep. 2013, vol. 90, pp. 25-31.

Lesmes L.A., et al., "Bayesian Adaptive Estimation of the Contrast Sensitivity Function: the Quick CSF Method," Journal of Vision, Mar. 2010, vol. 10 (3) 17, pp. 1-21.

Morlock, R., et al., "Patient-Reported Spectacle Independence Questionnaire (PRSIQ): Development and Validation," American Journal of Ophthalmology, Jun. 2017, vol. 178, pp. 101-114.

Ortiz, C., et al., "Quantification and Monitoring of Visual Disturbances for patients with cataracts using Halo v1.0 software," Department of Optics, Laboratory of Vision Sciences and Applications, University of Granada, IWBBIO 2013, Mar. 20, 2013, XP055596332, Proceedings, 8 Pages.

Rosen R., et al., "A Bayesian Method Using through Focus Visual Acuity to Predict Rates of Spectacle Wear for Pseudophakic patients," Investigative Ophthalmology & Visual Science, Jul. 2018, vol. 59 (9), pp. 1075, ARVO Annual Meeting Abstract, Retrieved from the Internet: (URL: https://iovs.arvojournals.org/article.aspx?articleid=2693341&resultClick=1).

Vitale S., et al., "The Refractive Status and Vision Profile: A Questionnaire to Measure Vision-Related Quality of Life in Persons with Refractive Error," Ophthalmology, Aug. 2000, vol. 107 (8), pp. 1529-1539.

Weeber H.A., et al., "Influence of Corneal Aberrations on Dysphotopsia with Multifocal IOLs," ARVO, 2011, Abstract.

Weeber H.A., et al., "Influence of Corneal Aberrations on Dysphotopsia with Multifocal IOLs," RD3115, 2011.

Weeber H.A., et al., "Optical and Visual Performance of Patient Populations Implanted with Monofocal and Multifocal IOLs in the Presence of Defocus," Investigative Ophthalmology & Visual Science, 2010, vol. 51, E-Abstract 5751.

Weeber H.A., et al., "Population-based Visual Acuity in the Presence of Defocus Well Predicted by Classical Theory," Journal of Biomedical Optics, 2010, vol. 15 (4), pp. 040509.

Weeber H.A., et al., "Theoretical Performance of Intraocular Lenses Correcting Both Spherical and Chromatic Aberration," Journal of Refractive Surgery, 2012, vol. 28 (1), pp. 48-52.

\* cited by examiner

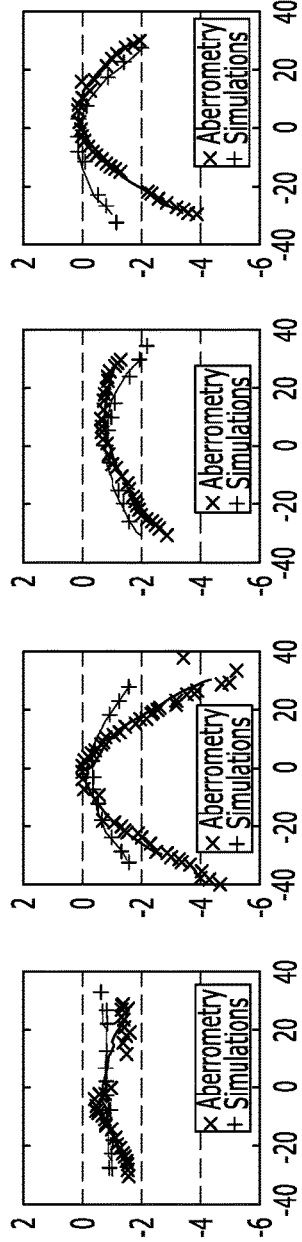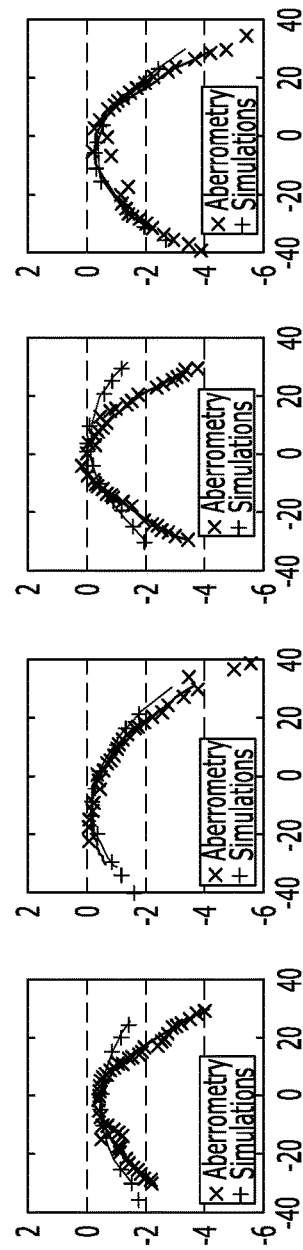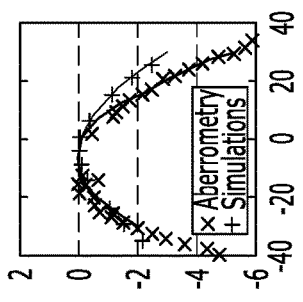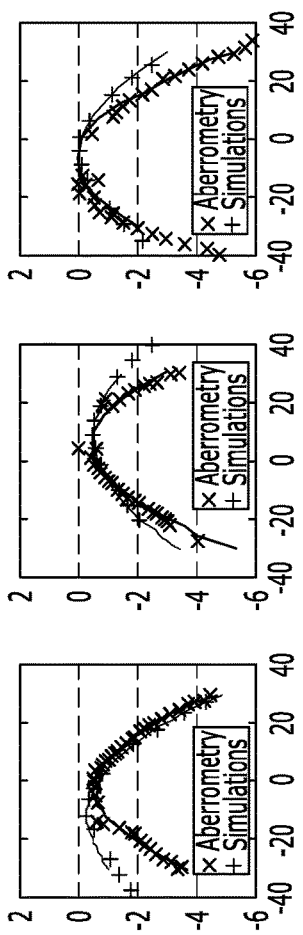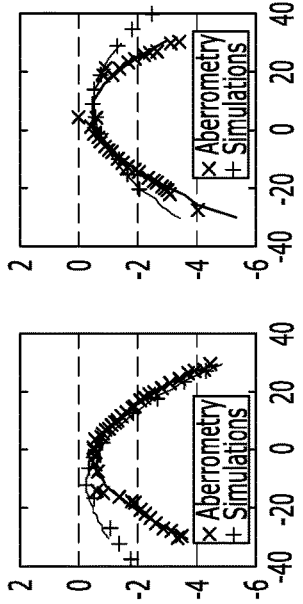

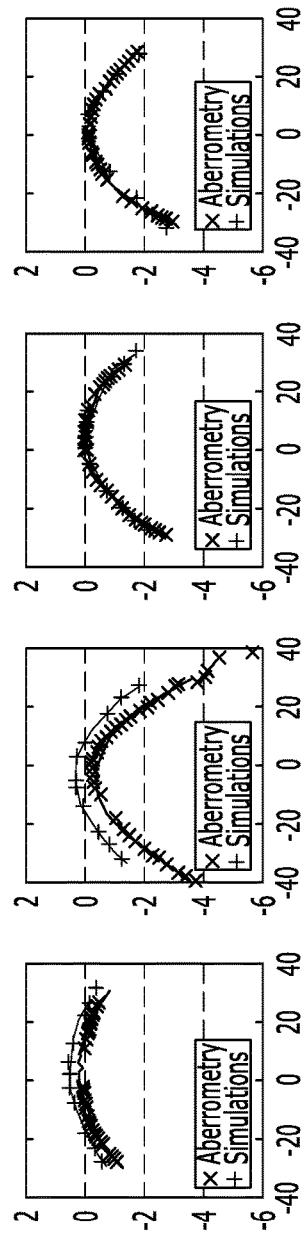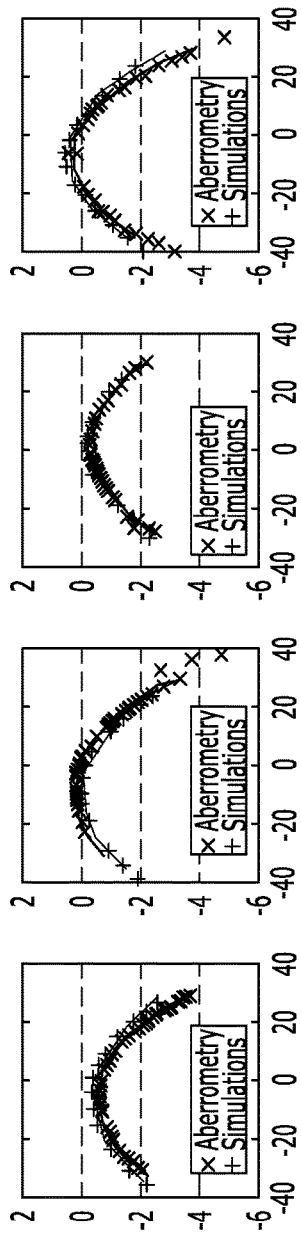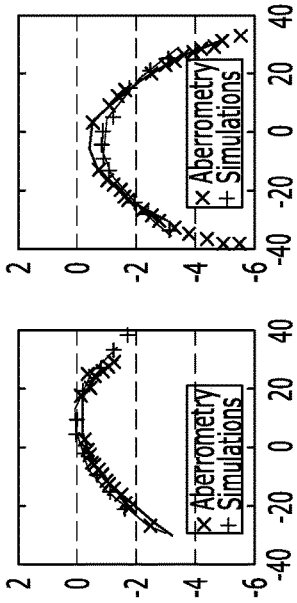

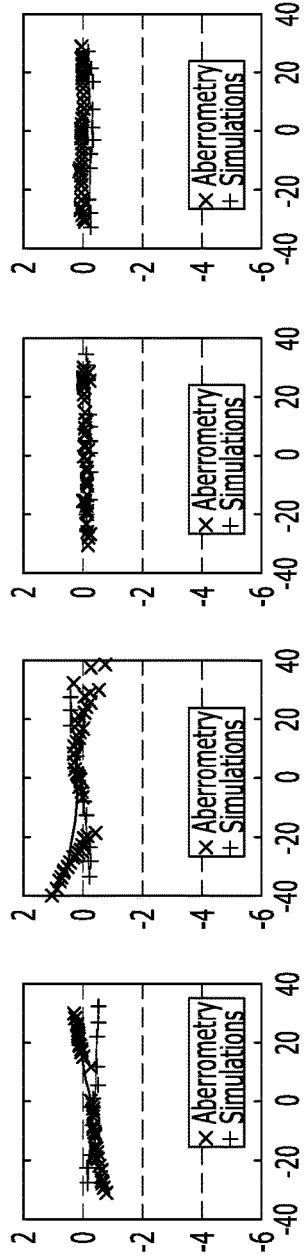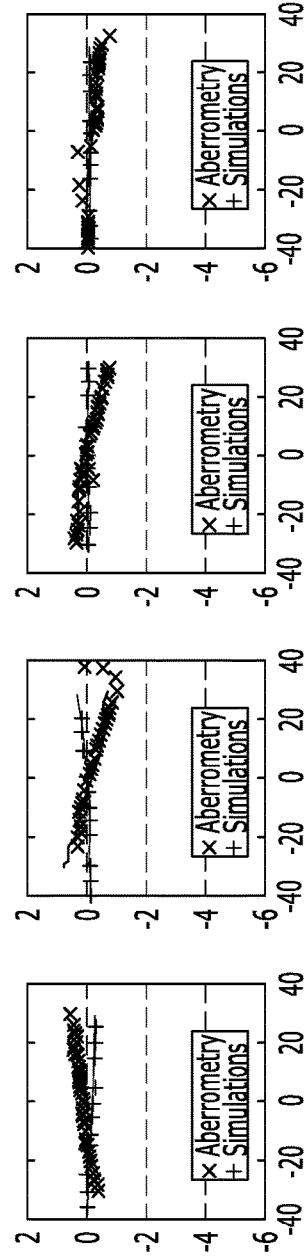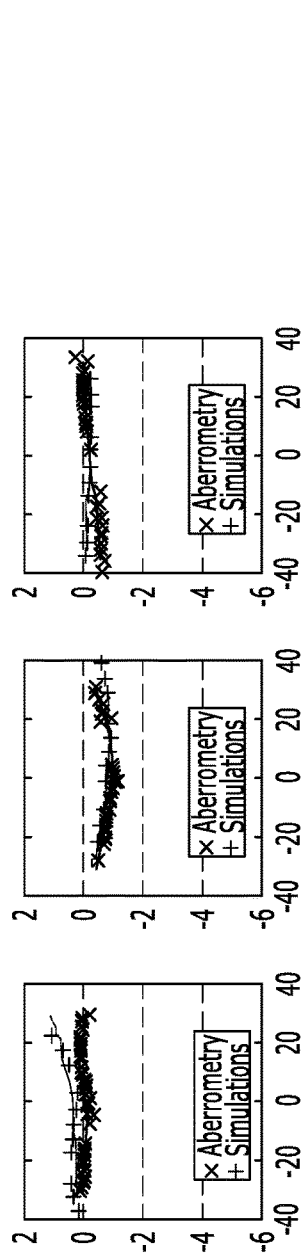

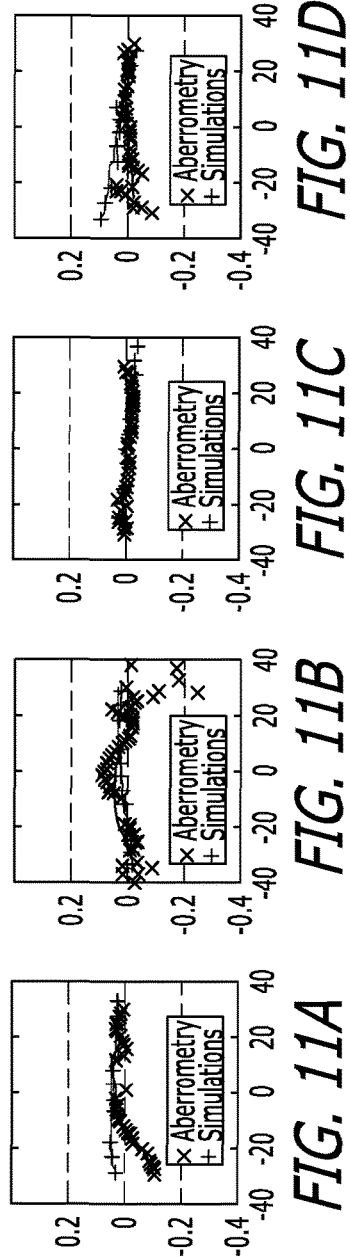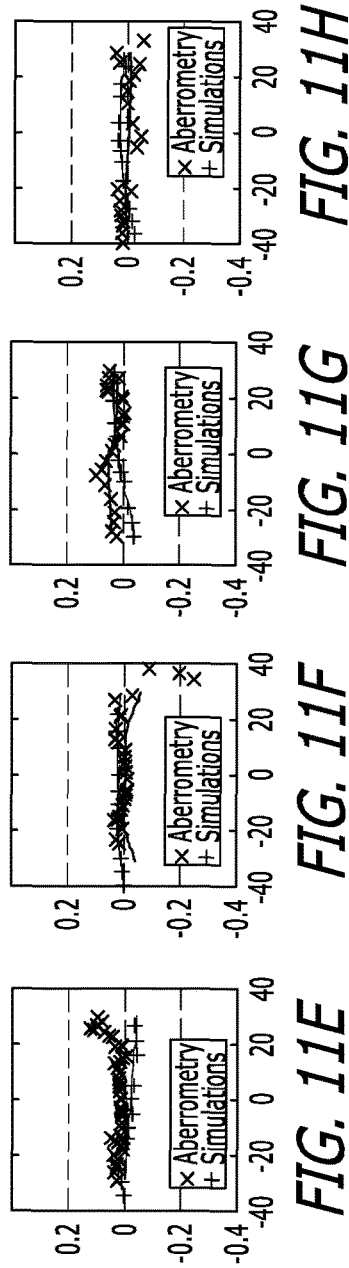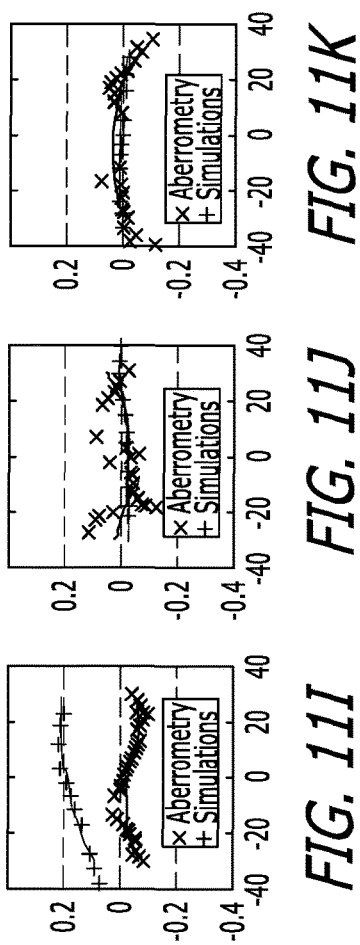

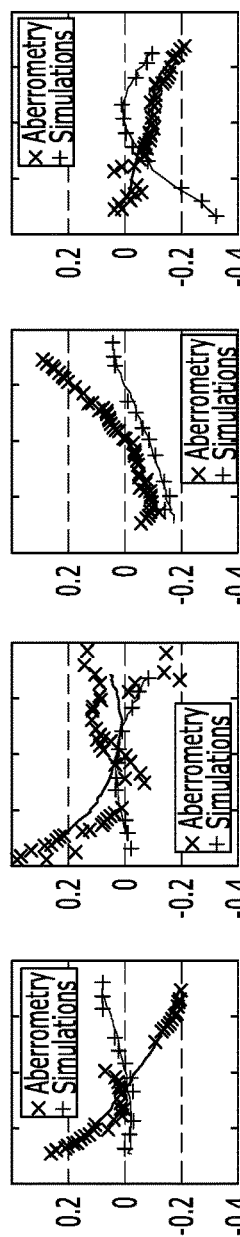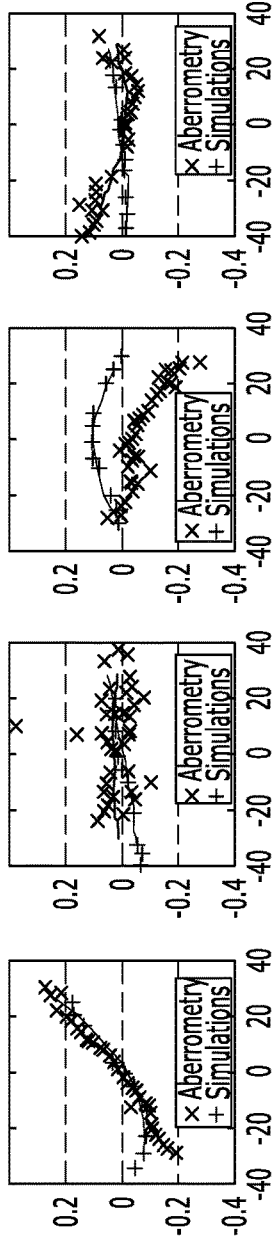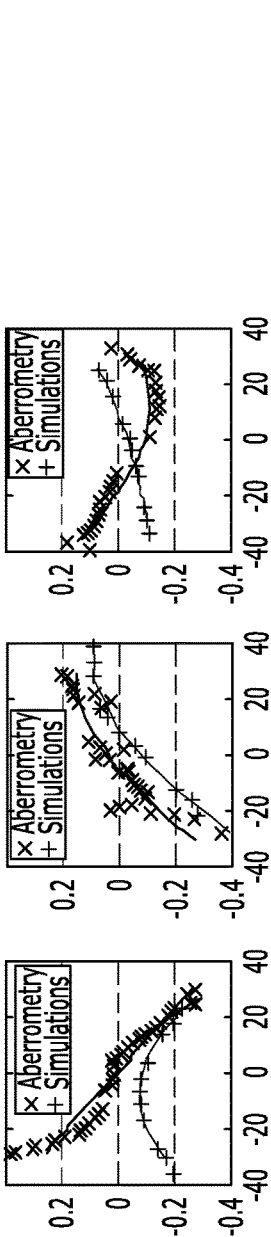
FIG. 12A FIG. 12B FIG. 12C FIG. 12D
FIG. 12E FIG. 12F FIG. 12G FIG. 12H
FIG. 12I FIG. 12J FIG. 12K

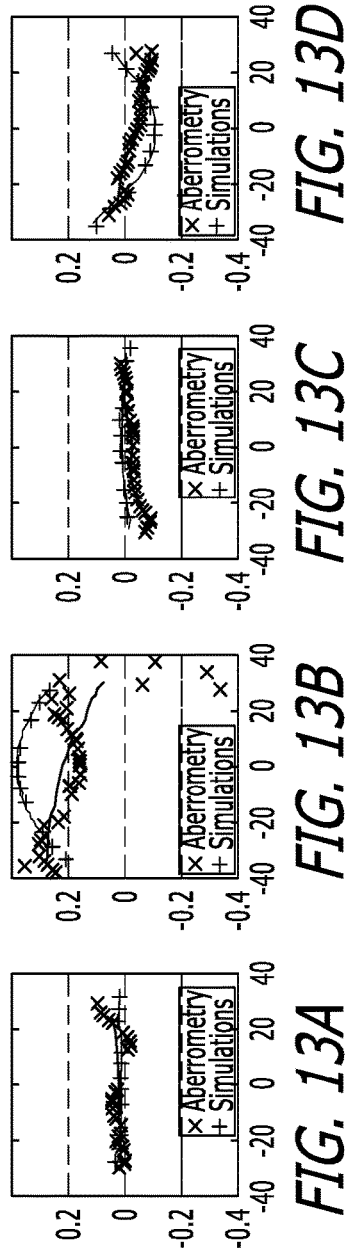
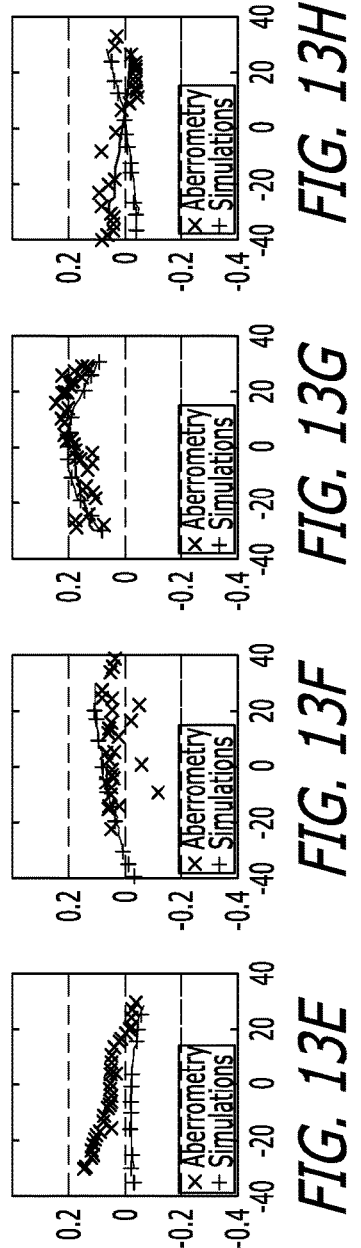
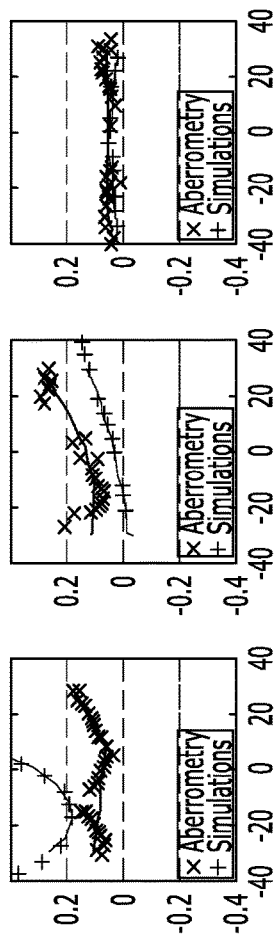
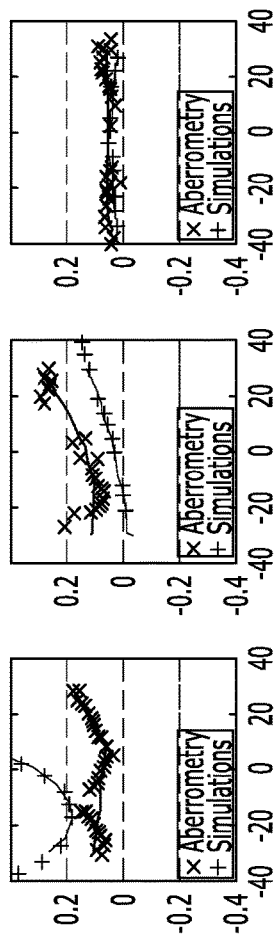
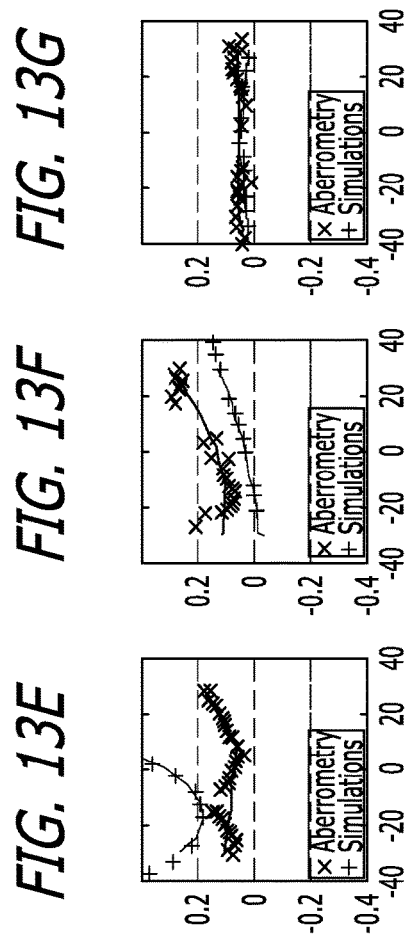
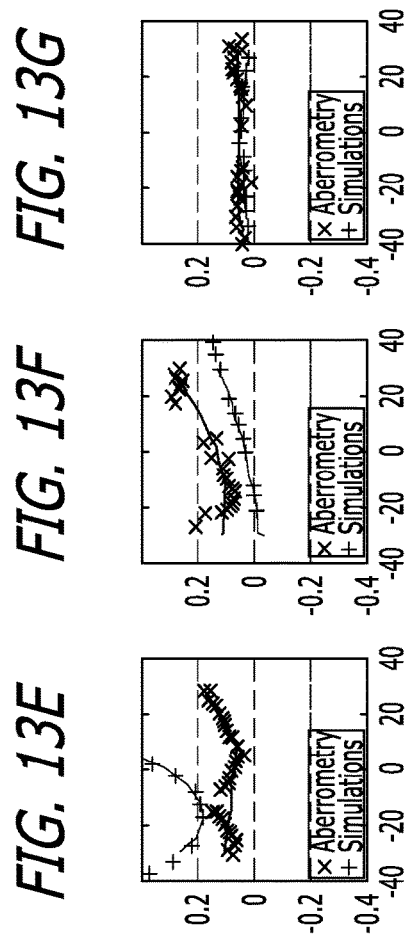

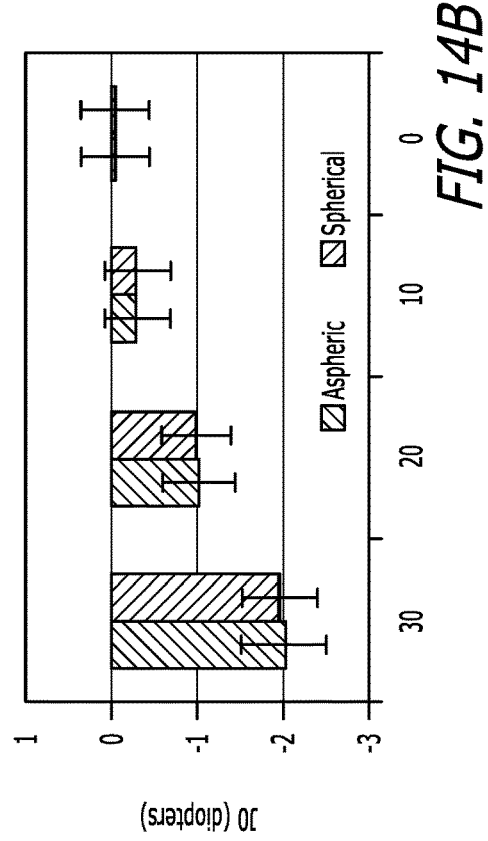
FIG. 14A
FIG. 14B
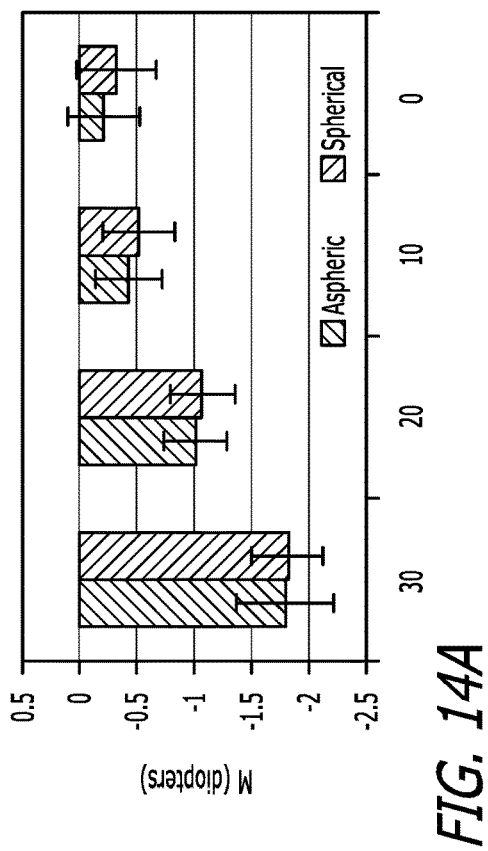
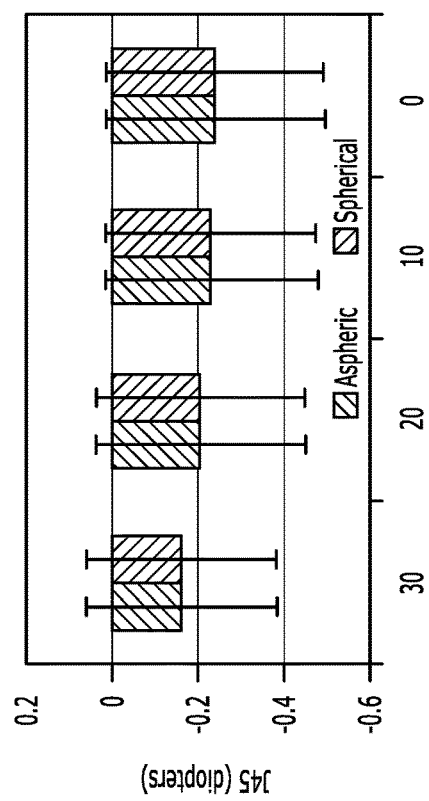
FIG. 14C

REALISTIC EYE MODELS TO DESIGN AND EVALUATE INTRAOCULAR LENSES FOR A LARGE FIELD OF VIEW

RELATED APPLICATIONS

This application claims priority to, and the benefit of, under U.S.C. § 119(e) of U.S. Provisional Appl. No. 62/412,738, filed on Oct. 25, 2016, which is incorporated herein by reference in its entirety.

FIELD OF THE INVENTION

The present invention relates generally to the field of lens design. More particularly, the present invention relates to a system, method, and apparatus for using a library of computer eye models to design and test intraocular lenses (IOLs) for improved peripheral and/or central visual field performance.

BACKGROUND OF THE INVENTION

Intraocular Lenses (IOLs) may be used for restoring visual performance after a cataract or other ophthalmic procedure in which the natural crystalline lens is replaced with or supplemented by implantation of an IOL. When the optics of the eye are changed by such a procedure, the goal is to improve vision in the central field. However, current IOL technology degrades peripheral optical quality, which is known to degrade peripheral visual performance. Degraded peripheral vision may be detrimental to many aspects of life, including increased risks for car crashes and falling.

One of the problems when looking for an optimal solution to correct peripheral aberrations is that peripheral aberrations are strongly dependent on the anterior corneal geometry and axial lengths (and therefore, on the foveal refractive state). Due to that, any design to correct peripheral aberration will perform differently depending on the foveal refractive state, corneal anterior geometry and axial lengths (anterior chamber depth and vitreous length).

Different eye models have been proposed to evaluate pre-clinically IOLs visual performance on axis and to design new IOLs based on the on-axis performance. However, these eye models usually have a fixed cornea and modify vitreous lengths to test IOLs with different optical powers. Also, these average eye models have not been used to test the periphery.

Thus, there is a need for new types of computer eye models to evaluate IOL performance. There is a further need for improved computer eye models to design new IOLs based on on-axis performance. There is an additional need for improved system, method, and apparatus for a library of computer eye models to design and test intraocular lenses (IOLs) that improve peripheral and central visual field performance, and to test the central and peripheral optical performance of new and existing IOL designs under more realistic conditions. There is a need for eye models that contain higher order cornea aberrations and different biometry and are validated for a large field of view (from +30 to −30 degrees of the visual field). The present invention satisfies these needs and provides other related advantages.

BRIEF DESCRIPTION OF THE DRAWINGS

The various present embodiments now will be discussed in detail with an emphasis on highlighting the advantageous features with reference to the drawings of various embodiments. The illustrated embodiments are intended to illustrate, but not to limit the invention. These drawings include the following figures, in which like numerals indicate like parts:

FIGS. 8A-8K illustrate eleven plots comparing simulated defocus (M) aberrations (+) and measured defocus (M) aberrations (x) for eleven different eye models;

FIGS. 9A-9K illustrate eleven plots comparing simulated astigmatism (J0) aberrations (+) and measured astigmatism (J0) aberrations (x) for eleven different eye models;

FIGS. 10A-10K illustrate eleven plots comparing simulated astigmatism (J45) aberrations (+) and measured astigmatism (J45) aberrations (x) for eleven different eye models;

FIGS. 11A-11K illustrate eleven plots comparing simulated spherical (SA) aberrations (+) and measured spherical (SA) aberrations (x) for eleven different eye models;

FIGS. 12A-12K illustrate eleven plots comparing horizontal coma aberrations (+) and measured horizontal coma aberrations (x) for eleven different eye models;

FIGS. 13A-13K illustrate eleven plots comparing vertical coma aberrations (+) and measured vertical coma aberrations (x) for eleven different eye models;

FIGS. 14A-14C illustrate histograms comparing the average aberrations provided by a spherical and an aspheric IOL between −30 and 30 degrees for lower order aberrations including defocus (M) and astigmatism (J0 and J45);

DETAILED DESCRIPTION OF THE INVENTION

Figure 1:
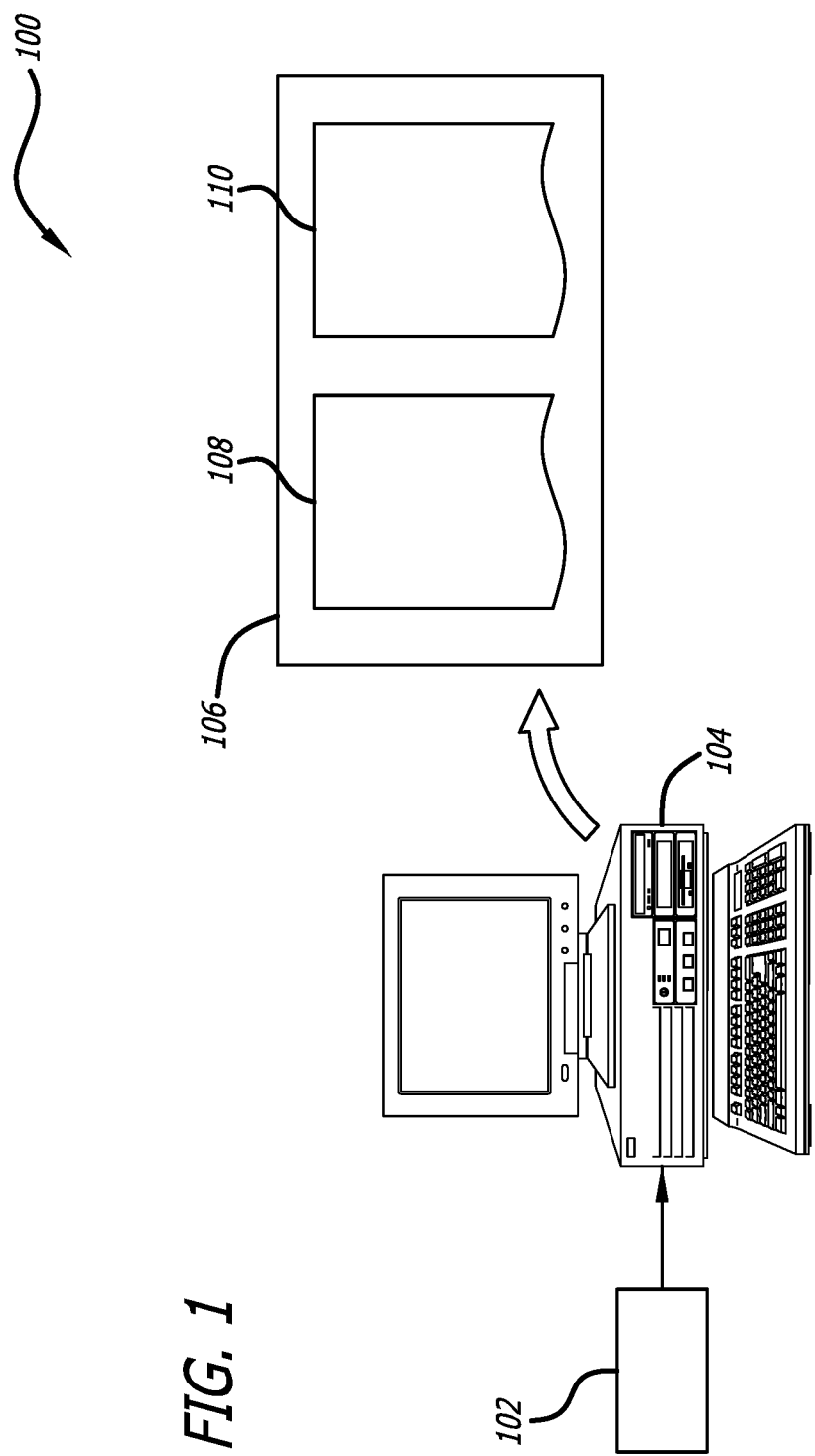
FIG. 1 illustrates a block diagram of a computerized implementation in accordance with an embodiment of the present invention.

The following detailed description describes the present embodiments, with reference to the accompanying drawings. In the drawings, reference numbers label elements of the present embodiments. These reference numbers are reproduced below in connection with the discussion of the corresponding drawing features.

It is to be understood that the figures and descriptions of the present invention have been simplified to illustrate elements that are relevant for a clear understanding of the present invention, while eliminating, for the purpose of clarity, many other elements found in typical lenses, lens systems and lens design methods. Those of ordinary skill in the pertinent arts may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the pertinent arts.

For normal patients (e.g., uncomplicated cataract patients), it is desirable to balance peripheral vision with good central vision in order to maximize overall functional vision. For those patients having a pathological loss of central vision, peripheral vision may be maximized, taking into account the visual angle where the retina is healthy. It is also understood that embodiments may be applied directly, or indirectly, to various IOLs including, for example, phakic IOLs and piggyback IOLs, as well as other types of ophthalmic lenses including, but not limited to, corneal implants, corneal surgical procedures such as LASIK or PRK, contact lenses, and other such devices. In some embodiments, various types of ophthalmic devices are combined, for example, an intraocular lens and a LASIK procedure may be used together to provide a predetermined visual outcome. Embodiments of the invention may also find particular use with spherical, aspheric, multifocal or accommodating intraocular lenses.

The present invention is directed to a library of computer eye models to design intraocular lenses (IOIs) that improve peripheral and central visual field performance, and to test the central and peripheral optical performance of new and existing IOL designs under more realistic conditions. In addition, the eye model(s) may also be used to design IOIs and other ophthalmic lenses, such as a phakic IOL or a corneal implant, and other vision correction methodologies, such as laser treatments, and a system and method relating to same, for providing improved peripheral and central visual field performance, and to test the central and peripheral optical performance of new and existing IOL designs under more realistic conditions.

The apparatus, system and method of the present invention may be predictive as to the performance of IOILs in the eye under any of a variety of circumstances, and with respect to any of a variety of ocular conditions and eye types, and may provide for improved performance of IOIs. For example, the present invention may include mathematical modeling of certain characterizations of the eye, such as total axial length of the eye (AL), cornea thickness (CT), anterior chamber depth (ACD), elevation map of the anterior cornea (Zemike Fit) and/or IOL Power, and comparison of model output to actual clinical data. It will be appreciated by those of ordinary skill in the pertinent arts that the apparatus, system and method of the present invention may be embodied in one or more computing processors, associated with one or more computing memories, within which is resident computing code to execute the mathematical models discussed herein, to provide the eye models discussed herein in a relational database to design and test ophthalmic lenses as part of the system, apparatus and method of the present invention. Further, those skilled in the art will appreciate, in light of the disclosure herein, that the aspects of the present invention may be provided to the one or more computing processors for processing via one or more computing networks, including via one or more nodes of a computing network. Computing networks for use in the present invention may include the Internet, an intranet, an extranet, a cellular network, a satellite network, a fiber optic network, or the like. Those skilled in the art might appreciate that all relevant measurements on what the present invention is based may be performed by using instruments known in the art. However, an instrument comprising all needed measurements (ocular and corneal wavefront aberration measurements) as well as the needed calculations to test and design IOLs can be considered an apparatus of the present invention.

An instrument can comprise a set of apparatuses, including a set of apparatuses from different manufacturers, configured to perform the necessary measurements and calculations. FIG. 1 shows a block diagram illustrating an implementation of the present invention in a system 100 comprised of one or more apparatuses capable of performing the calculations, assessments and comparisons discussed herein. The system 100 may include a biometric reader/simulator and/or like input 102, a processor 104, and a computer readable memory or medium 106 coupled to the processor 104. The computer readable memory 106 includes therein an array of ordered values 108 and sequences of instructions 110 which, when executed by the processor 104, cause the processor 104 to select and/or design the aspects discussed herein for association with a lens to be implanted into the eye, or reshaping to be performed on the eye, subject to the biometric readings/simulation at input 102. The array of ordered values 108 may comprise data used or obtained from and for use in design methods consistent with embodiments of the invention. The sequence of instructions 110 may include one or more steps consistent with embodiments of the invention. In some embodiments, the sequence of instructions 110 includes applying calculations, customization, simulation, comparison, and the like.

The processor 104 may be embodied in a general purpose desktop, laptop, tablet or mobile computer, and/or may comprise hardware and/or software associated with inputs 102. In certain embodiments, the system 100 may be configured to be electronically coupled to another device, such as one or more instruments for obtaining measurements of an eye or a plurality of eyes. Alternatively, the system 100 may be adapted to be electronically and/or wirelessly coupled to one or more other devices.

The system 100 can be adapted for designing and evaluating intraocular lenses for a large field of view, comprising: a plurality of eye models based upon a first intraocular lens, associated with at least one processor 104, where each eye model of the plurality of eye models includes at least one aberration. A simulator provided by the at least one processor 104 that models a second intraocular lens in at least one of the plurality of eye models, where the simulator outputs at least one aberration of the second intraocular lens in the at least one of said plurality of eye models. A comparator instantiated by the at least one processor 104 compares differences between the aberrations of the first intraocular lens and the second intraocular lens.

Figure 2:
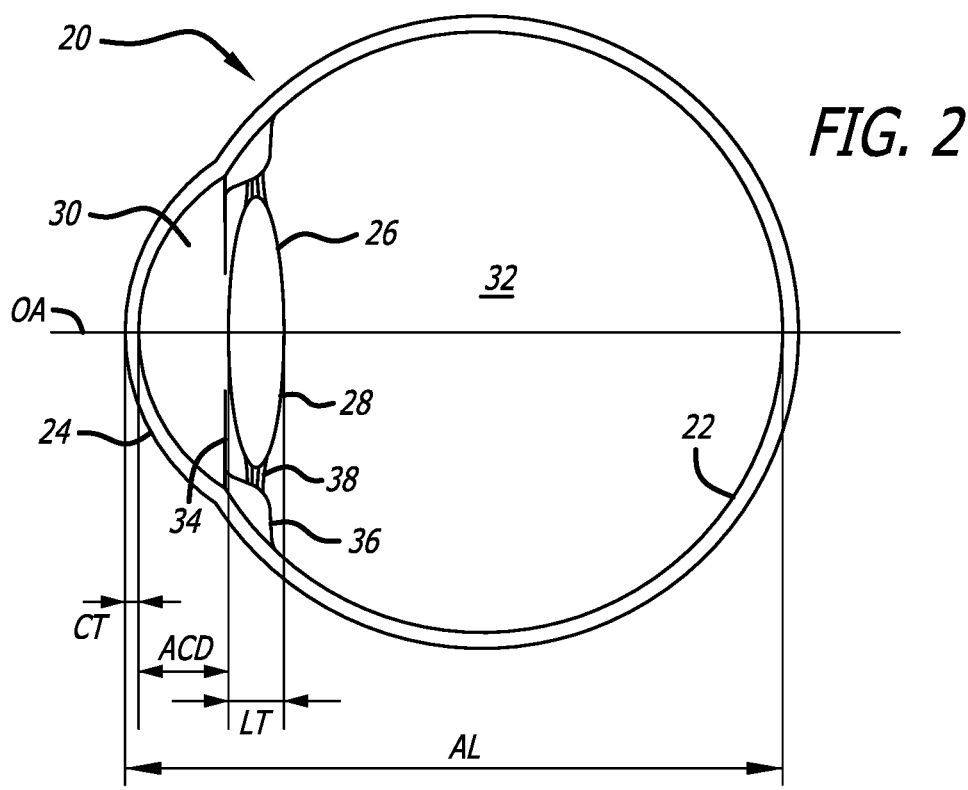
FIG. 2 illustrates an eye in a natural state.

FIG. 2 is an illustration of an eye 20 in a natural state. The eye 20 includes a retina 22 for receiving an image, produced by light passing through a cornea 24 and a natural lens 26, from light incident upon the eye 20. The natural lens 26 is disposed within a capsular bag 28, which separates anterior and posterior chambers 30, 32 of the eye 20. An iris 34 may operate to change the aperture, i.e. pupil, size of the eye 20. More specifically, the diameter of the incoming light beam is controlled by the iris 34, which forms the aperture stop of the eye 20. An optical axis OA is defined by a straight line perpendicular to the front of the cornea 24 of the eye 20 and extending through a center of the pupil.

The capsular bag 28 is a resilient material that changes the shape and/or location of natural lens 26 in response to ocular forces produced when ciliary muscles 36 contract and stretch the natural lens 26 via zonules 38 disposed about an equatorial region of the capsular bag 28. This shape change may flatten the natural lens 26, thereby producing a relatively low optical power for providing distant vision in an emmetropic eye. To produce intermediate and/or near vision, ciliary muscles 36 contract, thereby relieving tension on the zonules 38. The resiliency of the capsular bag 28 thus provides an ocular force to reshape the natural lens 26 to modify curvature to provide an optical power suitable for required vision. This change, or "accommodation," is achieved by changing the shape of the crystalline lens. Accommodation, as used herein, includes the making of a change in the focus of the eye for different distances.

Light enters the eye 20 from the left of FIG. 2, and passes through the cornea 24, the anterior chamber 30, the iris 34 through the pupil, and enters the lens 26. After passing through the lens 26, light passes through the posterior chamber 32, and strikes the retina 22, which detects the light and converts it to a signal transmitted through the optic nerve to the brain (not shown). The cornea 24 has a corneal thickness (CT), which is the distance between the anterior and posterior surfaces of the center of the cornea 24. The anterior chamber 30 has an anterior chamber depth (ACD), which is the distance between the posterior surface of the cornea 24 and the anterior surface of the lens 26. The lens 26 has a lens thickness (LT) which is the distance between the anterior and posterior surfaces of the lens 26. The eye 20 has a total axial length (AL) which is the distance between the center of the anterior surface of the cornea 24 and the fovea of the retina 22, where the image should focus.

The anterior chamber 30 is filled with aqueous humor, and optically communicates through the lens 26 with the vitreous or posterior chamber 32, which occupies the posterior % or so of the eyeball and is filled with vitreous humor. The average adult eye has an ACD of about 3.15 mm, although the ACD typically shallows by about 0.01 mm per year. Further, the ACD is dependent on the accommodative state of the lens 26 (i.e., whether the lens 26 is focusing on an object that is near or far).

Figure 3:
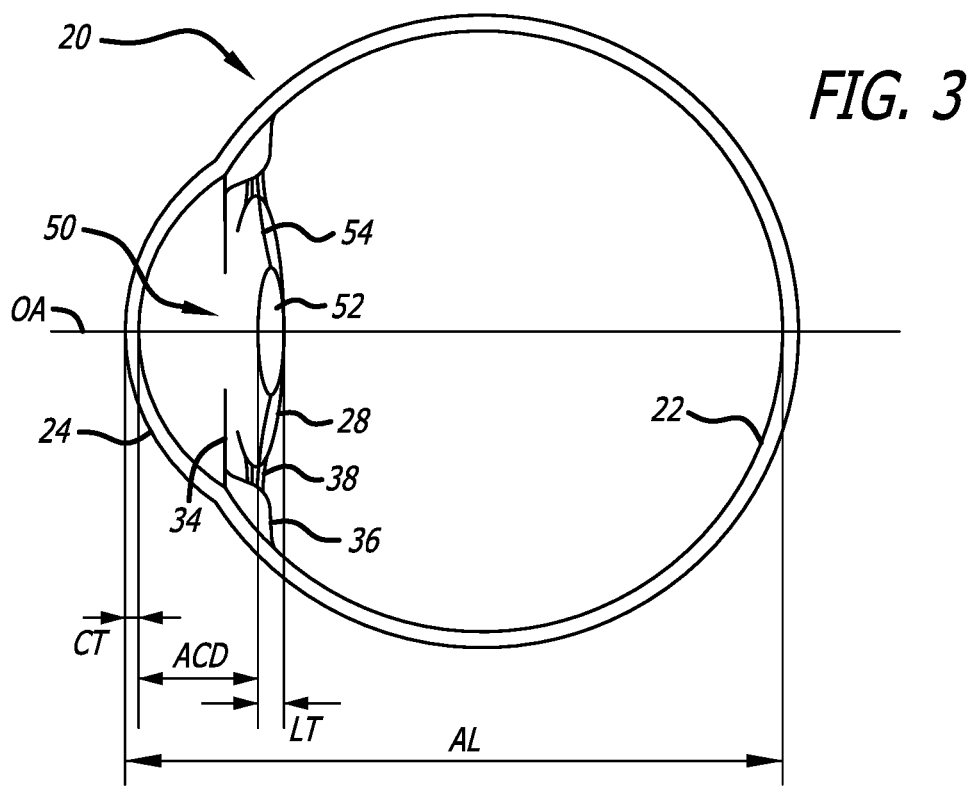
FIG. 3 illustrates an eye having an intraocular lens.

FIG. 3 illustrates the eye 20 where the natural lens 26 has been replaced with an IOL 50. The natural lens 26 may have required removal due to a refractive lens exchange, or due to a disease such as cataracts, for example. Once removed, the natural lens 26 may have been replaced by the IOL 50 to provide improved vision in the eye 20. The eye 20 may include the IOL 50, where the IOL 50 includes an optic 52, and haptics or support structure 54 for centering the optic 52. The haptics 54 may center the optic 52 about the OA, and may transfer ocular forces from the ciliary muscle 32, the zonules 34, and/or the capsular bag 28 to the optic 52 to change the shape, power, and/or axial location of the optic 52 relative to the retina 22.

The terms "power" or "optical power" are used herein to indicate the ability of a lens, an optic, an optical surface, or at least a portion of an optical surface, to redirect incident light for the purpose of forming a real or virtual focal point. Optical power may result from reflection, refraction, diffraction, or some combination thereof and is generally expressed in units of Diopters. One of skill in the art will appreciate that the optical power of a surface, lens, or optic is generally equal to the reciprocal of the focal length of the surface, lens, or optic, when the focal length is expressed in units of meters.

The term "near vision," as used herein, refers to vision provided by at least a portion of a lens 26 or an IOL 50, wherein objects relatively close to the subject are substantially in focus on the retina of the subject eye. The term "near vision" generally corresponds to the vision provided when objects are at a distance from the subject eye of between about 25 cm to about 50 cm. The term "distance vision" or "far vision," as used herein, refers to vision provided by at least a portion of the lens 26 or IOL 50, wherein objects relatively far from the subject are substantially in focus on the retina of the eye. The term "distance vision" generally corresponds to the vision provided when objects are at a distance of at least about 2 m or greater. The term "intermediate vision," as used herein, refers to vision provided by at least a portion of a lens, wherein objects at an intermediate distance from the subject are substantially in focus on the retina of the eye. Intermediate vision generally corresponds to vision provided when objects are at a distance of about 2 m to about 50 cm from the subject eye. The term "peripheral vision," as used herein, refers to vision outside the central visual field.

A library of computer eye models is created to design new IOLs that improve peripheral and central visual field performance. These computer eye models are also used to test the central and peripheral optical performance of new and existing IOL designs under more realistic conditions. Elements of an eye model include anterior surface of the cornea (based on biometry data with topography data fitted to Zernike polynomials for a 6 mm central zone), posterior surface of the cornea, anterior lens (defined by IOL power), posterior lens (defined by IOL power), and the retina. These computer eye models are based on the following distances: total axial length (AL) (based on biometry data); cornea thickness (CT) (based on biometry data); anterior chamber depth (ACD) (optimized using the post-operative refraction); and lens thickness (LT) (defined by the IOL power). These eye models also include constant values and customized values. The constant values (i.e., similar for all eyes) include the posterior cornea and the retina 22. The customized values (i.e., different for each eye model) include the anterior cornea, and the anterior and posterior surfaces of the lens or lenses for dual optic systems.

Figure 5:
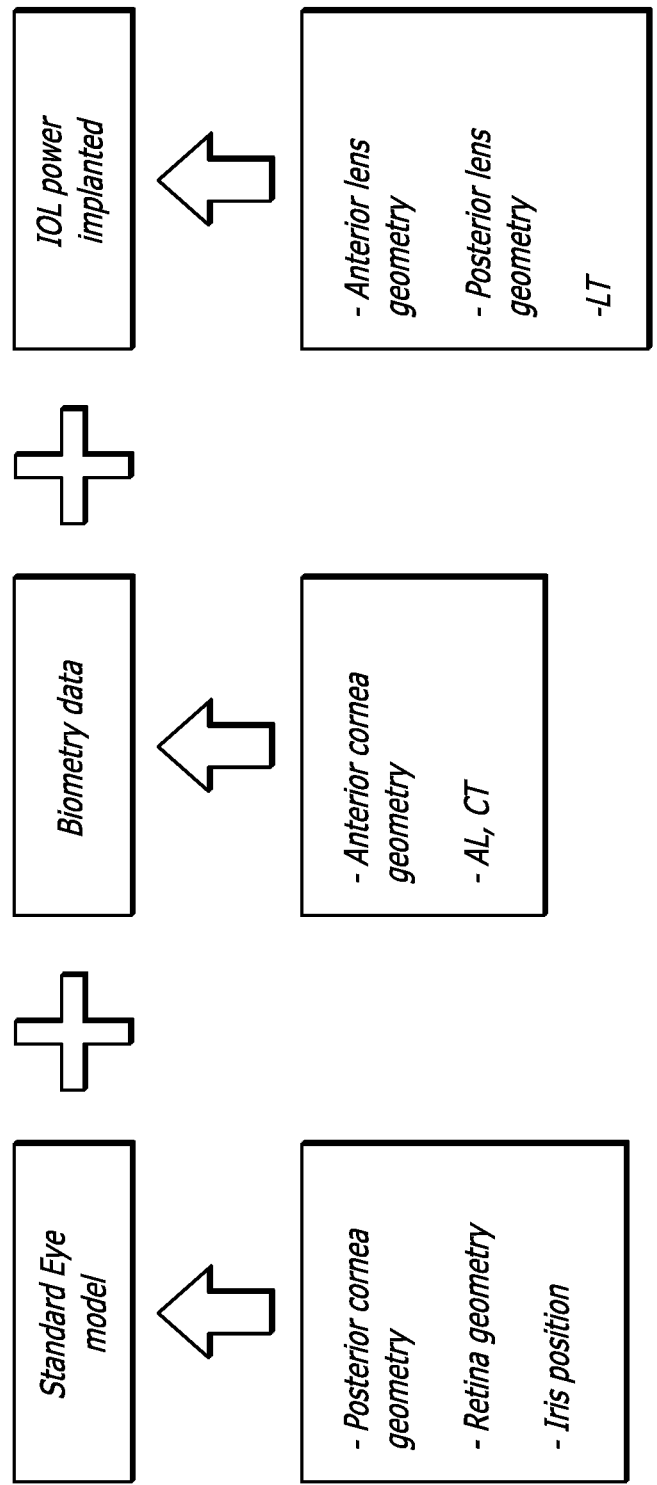
FIG. 5 illustrates a process flow to create an eye model.

FIG. 5 illustrates a process flow to create an eye model constructed using biometric data of real patients implanted with a monofocal TECNIS model ZCB00, one-piece Acrylic IOL from Abbott Medical Optics. The wavefront aberrations were measured post-operatively using a scanning aberrometer for 4 mm pupil and an eccentricity range of ±30 degrees. For example, the present invention may include mathematical modeling of certain characterizations of the eye, such as total axial length of the eye (AL), cornea thickness (CT), anterior chamber depth (ACD), elevation map of the anterior cornea (Zernike Fit) and/or IOL Power that will enable eventual comparison of model output to actual measured data.

A process to create an eye model starts with standard eye model data ("standard" in the sense that the particular values are similar for all eye models) in combination with biometry data and IOL power of an implanted IOL. The standard eye model is calculated based on data relating to posterior cornea geometry, retina geometry, and iris position (i.e., constant values that are similar for all eye models). The biometry data (i.e., customized values that are different for each eye model) is calculated based upon data relating to anterior cornea geometry, axial length AL, and cornea thickness CT. The implanted IOL power (i.e., customized values that are different for each eye model) is calculated based upon anterior lens geometry, posterior lens geometry, and lens thickness LT. The implanted IOL power of the patient is known. If the power is not accurate after the procedure, it is assumed that the person is correctly refracted by wearing spectacles to correct for on-axis errors. Thus, the power on-axis is set to zero, and the peripheral refractive power has the value added or subtracted accordingly.

Figure 6:
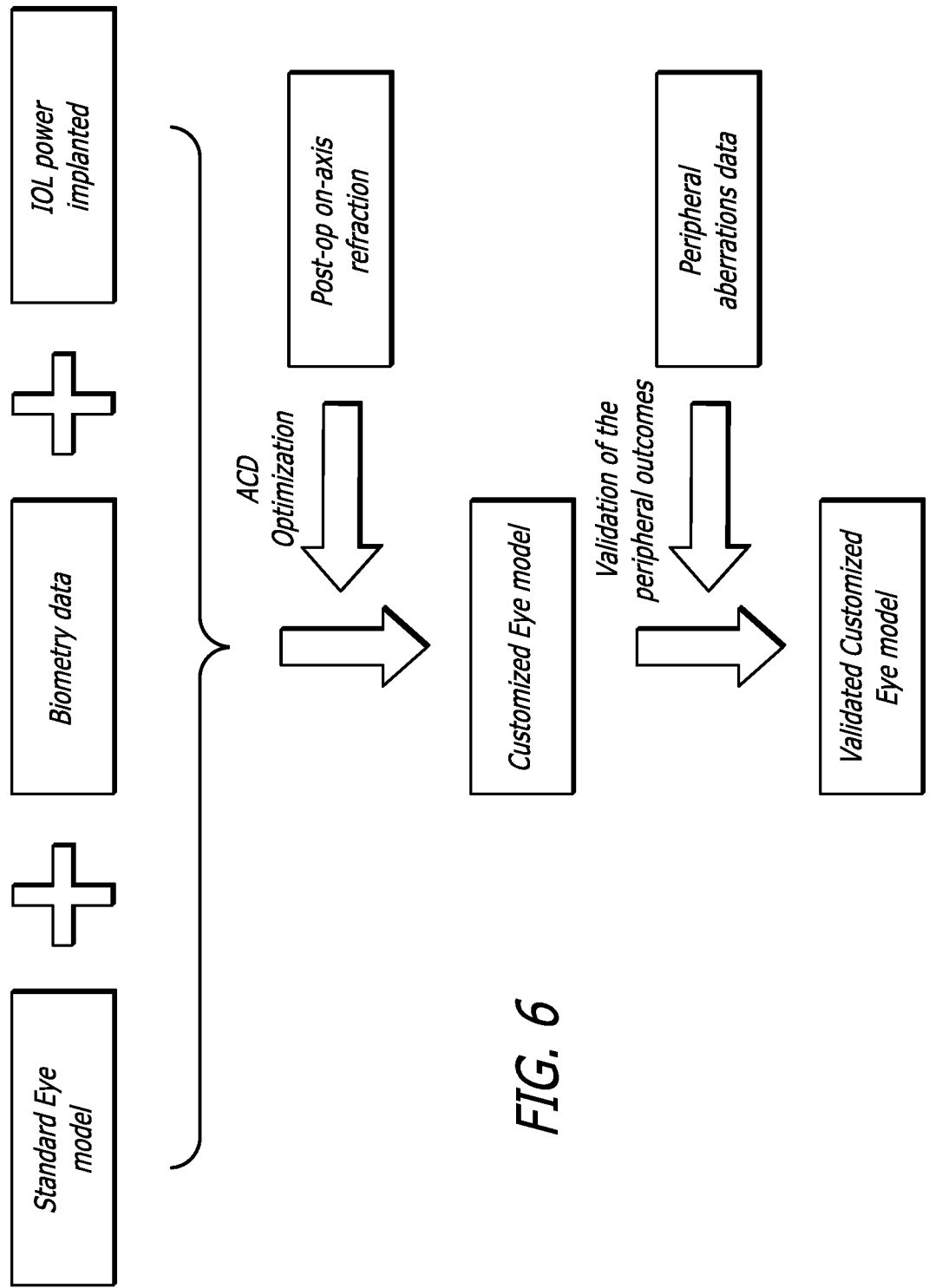
FIG. 6 illustrates a process flow to create a validated and customized eye model.

FIG. 6 illustrates a process flow to create a validated and customized eye model. A validated customized eye model is obtained using data from combination of data relating to the standard eye model, biometry data, and IOL Data relating to post-op on-axis refraction is obtained, and anterior chamber depth ACD optimized to arrive at a customized eye model. Validation of the peripheral outcomes from the customized eye model is achieved by comparison with peripheral aberrations data, which results in a validated, customized eye model.

Figure 7:
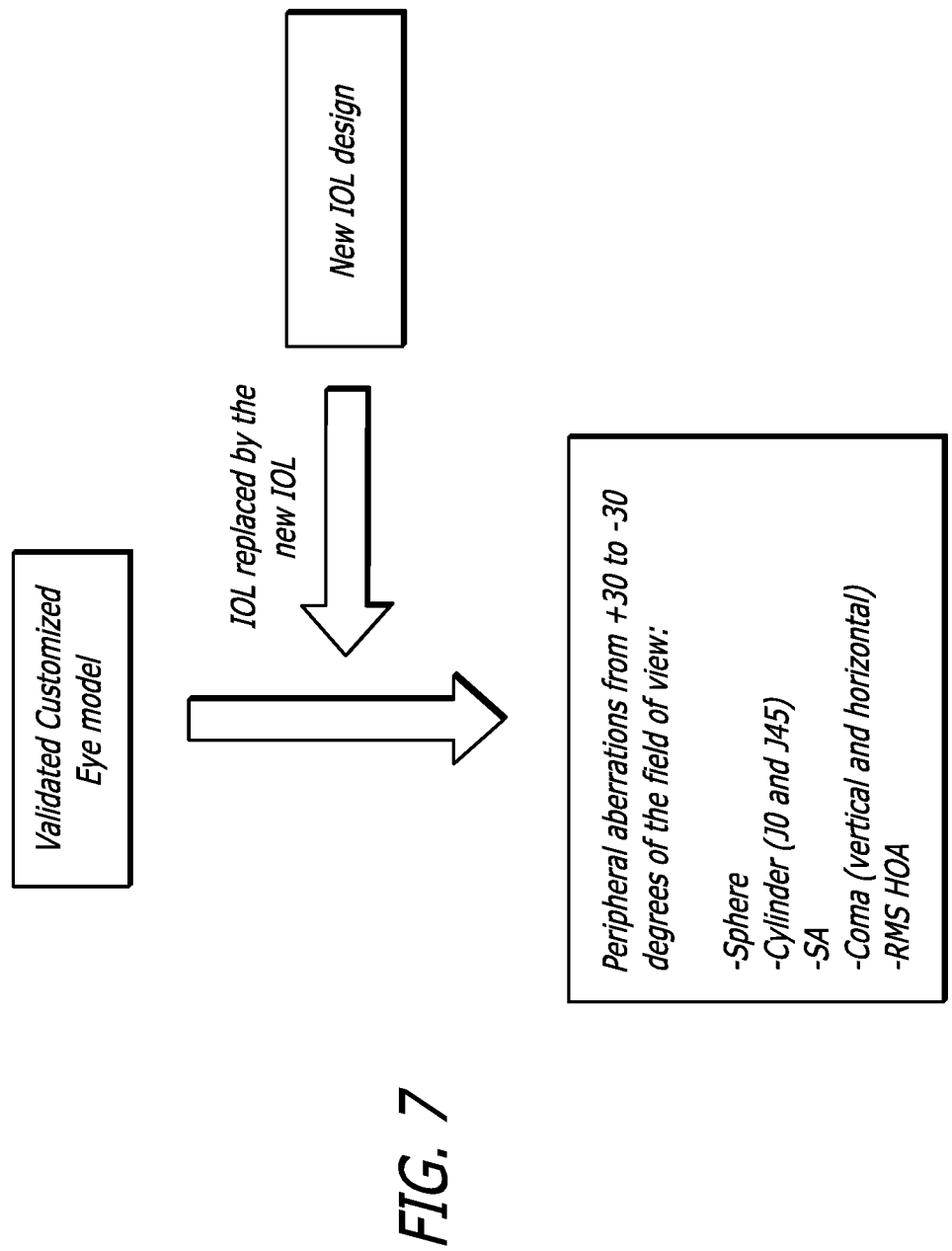
FIG. 7 illustrates a process flow to test a new IOL model.

FIG. 7 illustrates a process flow to test a new IOL model. An IOL in a validated customized eye model is replaced by a new IOL This new IOL can be a new IOL design that is being tested to address one or more issues relating to vision (e.g., peripheral aberrations). The peripheral aberrations from +30 to −30 degrees of the field of view are determined. These peripheral aberrations include sphere, cylinder (J0 and J45), spherical aberration SA, coma (vertical and horizontal), and root mean square higher order aberrations RMS HOA. The foregoing process can be applied to all the eye models resulting in an average performance of the IOL defined by the peripheral aberrations.

By way of non-limiting example, the embodiments herein are based on data from eleven (11) patients. Each patient has a particular eye model based on patient and existing biometries. For the eleven patients, eleven different eye models are created. For each of the eleven different eye models, a particular IOL design is "plugged in," and that same specific IOL design is tested at various diopters (e.g., 17.5, 19.5, 22, 23, etc.). Each power generates an output (e.g., a refractive error). A database is created that includes each eye model with the simulated outcomes provided by the particular IOL design. A database can be built-up to include as many eye models as desired. In this manner, one can review the results obtained from one lens design over a range of powers to see how that particular lens design behaves in a population. Then, a new IOL design may be plugged in and can compared to the prior IOL design. In this manner, feedback is provided to obtain data showing which specific IOL design provides the best result for an eye having particular biometries.

As seen in the illustrative examples of FIGS. 8A-13K, eleven (11) eye models were constructed using biometric data of real patients implanted with a monofocal TECNIS model ZCB00, one-piece Acrylic IOL from Abbott Medical Optics. However, any number of eye models can be created using biometric data of real patients implanted with a particular type of IOL. The wavefront aberrations were measured post-operatively using a scanning aberrometer for 4 mm pupil and an eccentricity range of ±30 degrees.

Figure 4:
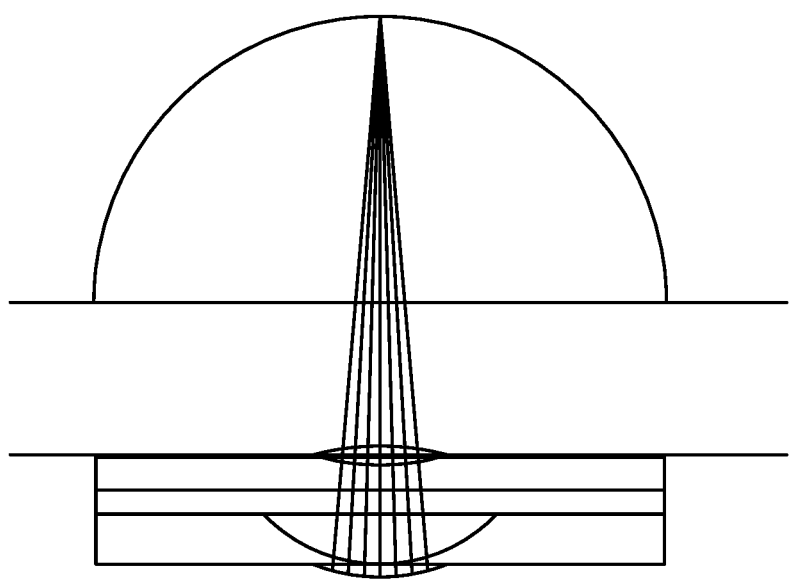
FIG. 4 illustrates an example of an eye modeling in ZEMAX.

The computer eye models provide a range of IOL powers tested between 19 and 24 Diopters (D) and each eye model is described by the following biometric parameters: total axial length of the eye (AL); cornea thickness (CT); anterior chamber depth (ACD); elevation map of the anterior cornea (Zernike Fit); and IOL Power. The foregoing information is used to create the eye models using ray tracing software (e.g., ZEMAX). All surfaces are centered with respect to the optical axis OA. As used herein, a ray tracing procedure is a procedure that simulates light propagation and refraction, by means of an exact solution of Snell's law, for all rays passing through an optical system. Those skilled in the art will appreciate that, for example, a ZEMAX optical design software simulation may be employed in order to provide ray tracing modeling for various aberrations of a realistic computer eye model. ZEMAX optical analysis software is manufactured by ZEMAX, LLC. This and other known optical modeling techniques, including Code V, OSLO, ASAP, and other software may also be used to create eye models. An example of an eye modeling in ZEMAX is shown in FIG. 4.

The above-mentioned eleven eye models can be associated with the processor 104, with a simulator (not shown) providing the input 102, as seen in FIG. 1. The simulator may be any type of modeling software capable of modeling an ophthalmic lens of a given design in at least one of the eye models provided. The simulator may be embodied as Code V, OSLO, ZEMAX, ASAP, and similar software modeling programs, for example. The processor 104 applies the input 102 from the simulator to at least one eye model to output a simulation of eye characteristics. As seen in Table 1, ZEMAX simulations showed that the realistic computer eye models are able to reproduce measured aberrations with an acceptable range of error. Table 1 shows the average error (plus or minus standard deviation) for eye models on-axis (0°), the off-axis absolute error between −30° and 30°, and the off-axis relative error between −30° and 30° (i.e., the off-axis relative error being the on-axis error subtracted from the off-axis absolute error) for the defocus (M) (measured in diopters), astigmatism (J0 and J45) (measured in diopters), and higher order aberrations (spherical aberrations (SA), horizontal coma (H-coma) and vertical coma (V-coma) (measured in microns)).

TABLE 1

| | M (diopters) | J0 (diopters) | J45 (diopters) | SA (microns) | H-coma (microns) | V-coma (microns) |
|---|---|---|---|---|---|---|
| On-axis | 0.03 ± 0.01 | 0.22 ± 0.21 | 0.11 ± 0.07 | 0.02 ± 0.01 | 0.09 ± 0.05 | 0.06 ± 0.07 |
| Off-axis relative | 0.57 ± 0.25 | 0.19 ± 0.14 | 0.25 ± 0.16 | 0.02 ± 0.01 | 0.03 ± 0.02 | 0.04 ± 0.02 |
| Off-axis absolute | 0.55 ± 0.24 | 0.30 ± 0.24 | 0.27 ± 0.15 | 0.03 ± 0.01 | 0.09 ± 0.04 | 0.07 ± 0.05 |

FIGS. 8A-8K illustrate eleven plots comparing simulated defocus (M) aberrations (+) and measured defocus (M) aberrations (x) for eleven different eye models.

FIGS. 9A-9K illustrate eleven plots comparing simulated astigmatism (J0) aberrations (+) and measured astigmatism (J0) aberrations (x) for eleven different eye models.

FIGS. 10A-10K illustrate eleven plots comparing simulated astigmatism (J45) aberrations (+) and measured astigmatism (J45) aberrations (x) for eleven different eye models.

FIGS. 11A-11K illustrate eleven plots comparing simulated spherical (SA) aberrations (+) and measured spherical (SA) aberrations (x) for eleven different eye models.

FIGS. 12A-12K illustrate eleven plots comparing horizontal coma aberrations (+) and measured horizontal coma aberrations (x) for eleven different eye models.

FIGS. 13A-13K illustrate eleven plots comparing vertical coma aberrations (+) and measured vertical coma aberrations (x) for eleven different eye models.

In a specific illustration, the realistic eye models herein presented can be used to estimate the optical performance of different IOLs at the periphery. For example, FIGS. 14A-

14C and 15A-15C compare the average aberrations provided by a spherical and an aspheric IOL between −30 and 30 degrees. No significant differences were found for defocus and astigmatism between the two IOL designs. However, as previously reported, the aspherical IOL significantly reduces SA for the range of eccentricities as well as the horizontal coma.

Figure 15B:
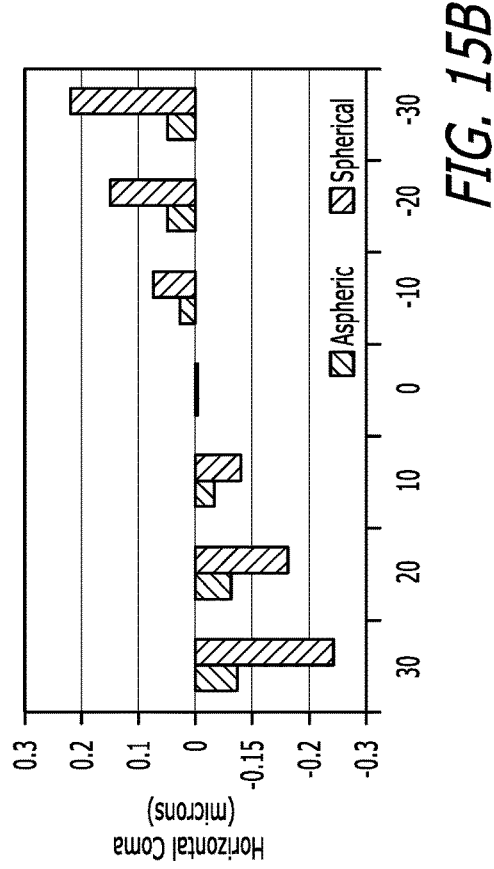
FIGS. 15A-15C illustrate histograms comparing the average aberrations provided by a spherical and an aspheric IOL between −30 and 30 degrees for higher order aberrations including spherical aberration (SA), horizontal coma, and vertical coma.
Figure 15A:
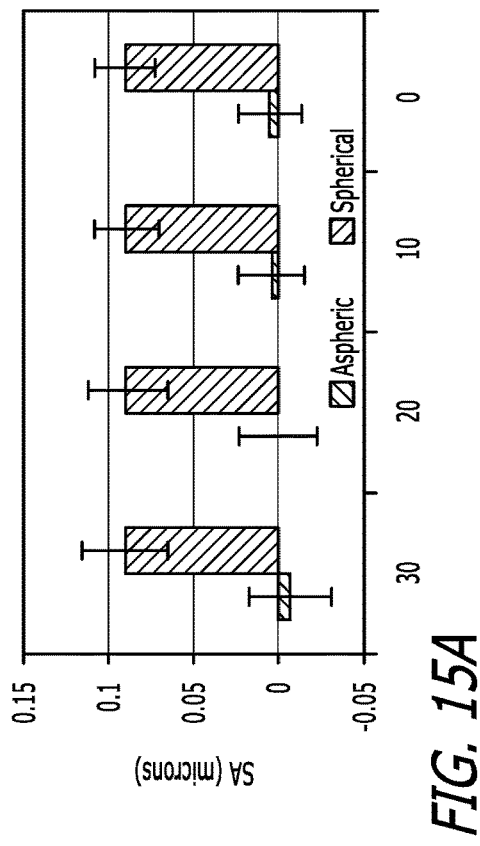
Figure 15C:
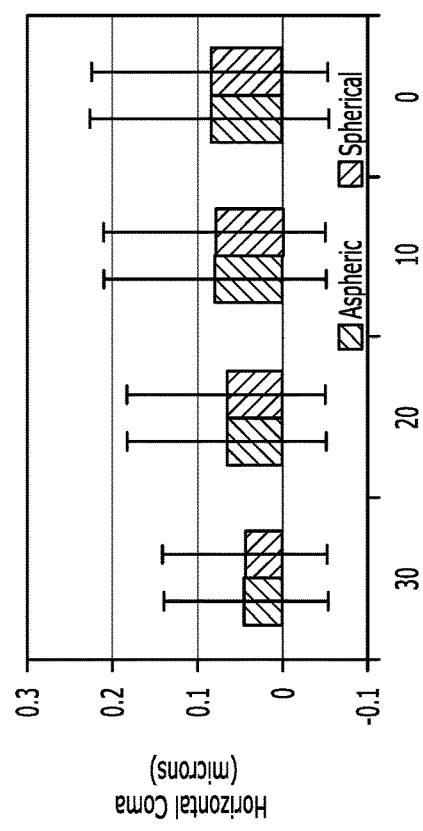

FIGS. 14A-14C illustrate histograms comparing the average aberrations provided by a spherical and an aspheric IOL between −30 and 30 degrees for lower order aberrations including defocus (M) and astigmatism (J0 and J45);

FIGS. 15A-15C illustrate histograms comparing the average aberrations provided by a spherical and an aspheric IOL between −30 and 30 degrees for higher order aberrations including spherical aberration (SA), horizontal coma, and vertical coma;

This library of realistic eye models can be also used to evaluate new IOL designs at the periphery. FIGS. 16A-16C and 17A-17C shows the average peripheral aberrations of an aspheric IOL and a new IOL design that theoretically reduces peripheral aberrations.

Figure 16A:
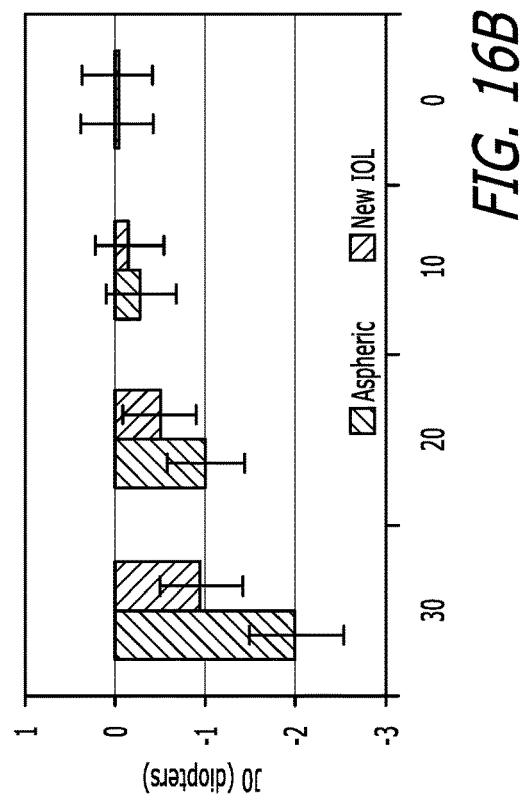
FIGS. 16A-16C illustrate histograms comparing the average peripheral aberrations of an aspheric IOL and a new IOL design that theoretically reduces peripheral aberrations for lower order aberrations including defocus (M) and astigmatism (J0 and J45)
Figure 16B:
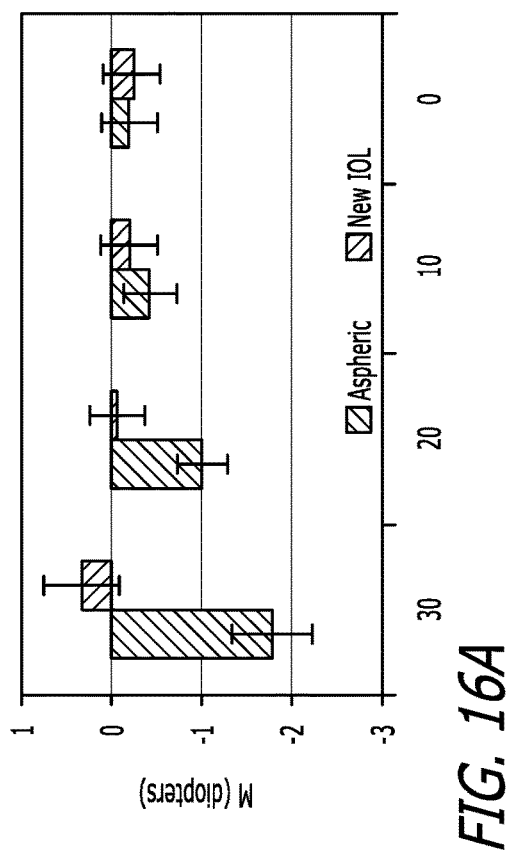
Figure 16C:
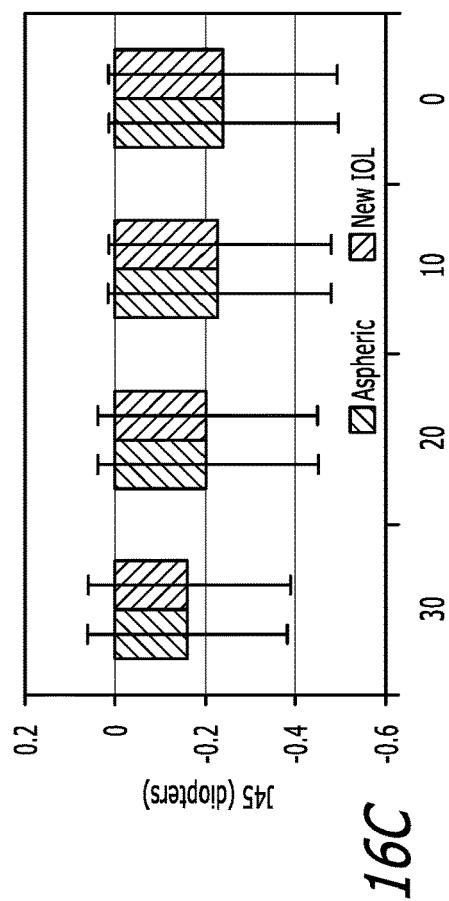

FIGS. 16A-16C illustrate histograms comparing the average peripheral aberrations of an aspheric IOL and a new IOL design that theoretically reduces peripheral aberrations for lower order aberrations including defocus (M) and astigmatism (J0 and J45).

Figure 17B:
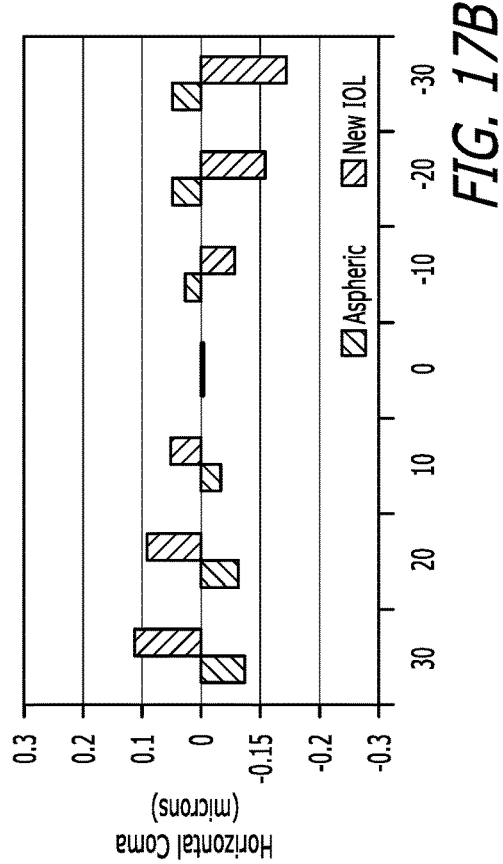
FIGS. 17A-17C illustrate histograms comparing the average peripheral aberrations of an aspheric IOL and a new IOL design that theoretically reduces peripheral aberrations for higher order aberrations including spherical aberration (SA), horizontal coma, and vertical coma.
Figure 17A:
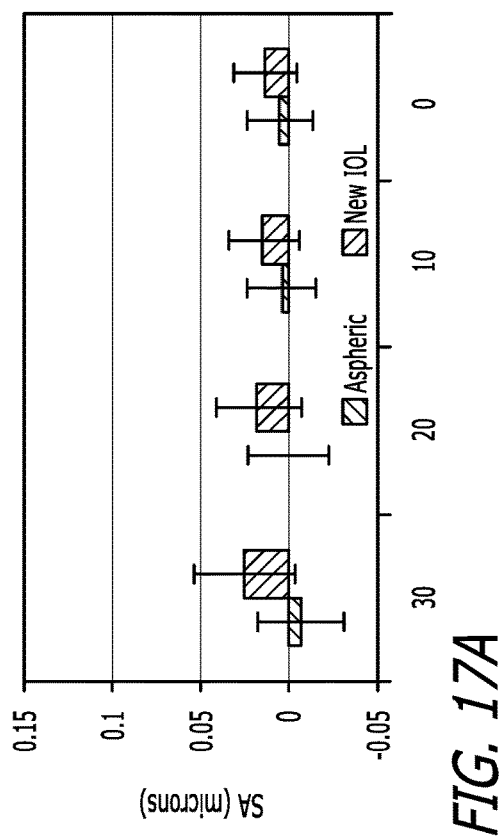
Figure 17C:
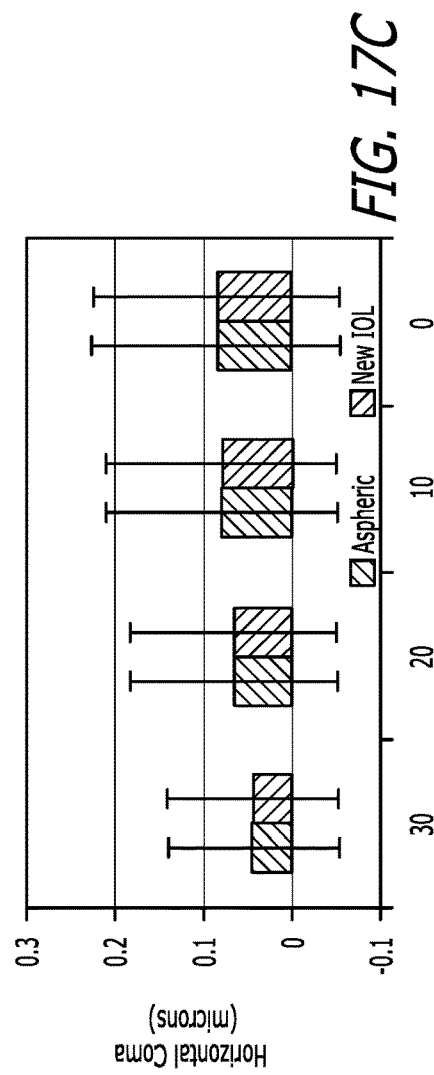

FIGS. 17A-17C illustrate histograms comparing the average peripheral aberrations of an aspheric IOL and a new IOL design that theoretically reduces peripheral aberrations for higher order aberrations including spherical aberration (SA), horizontal coma, and vertical coma.

Simulations showed that the new IOL can reduce M and J0 at the periphery without modifying J45 and vertical coma. Simulations also shows that there is a minimal increment in SA and an increment in horizontal coma that has opposite sign that the one induced by the spherical lens.

There may be additional alternative embodiments. For example, the designed eye models can also include the different axes of the eye, incorporating the shift of the fovea relative to the cornea, pupil and IOL. In another example, the eye models can be used to predict chromatic properties, including longitudinal chromatic aberrations, chromatic shift of aberrations and transverse chromatic aberrations. In a further example, the eye models can simulate a realistic range of pupillary conditions. The eye models can include changes that happen when the eyes converge (e.g. pupillary shift).

In the alternative, the schematic eye models herein proposed can be used to test any existing IOL design (e.g., monofocal, multifocal, extended range of vision, or the like) and to optimize new ones. In another alternative, the schematic eye models herein proposed can be used to test corneal refractive procedures, add on lenses or spectacles. As mentioned, the schematic eye models herein proposed can be used for ray tracing simulations. The geometry of the schematic eye models herein proposed can be used to build physical eye models. The schematic eye models could also be used to predict on-axis VA and peripheral CS. The method described herein can be used to customize lens design for any patient.

Needless to say the illustrations immediately hereinabove are provided by way of example only, and may be applicable to lens design, modification of physical lens design, modification to simulation, modification to selections of eye models, and the like. Similarly, the illustrations are applicable to not only groups of patients, or with regard to current lens designs, but is equally applicable to custom and quasi-custom lens design, for individual patients and limited or unique subsets of patients, respectively.

In addition, the claimed invention is not limited in size and may be constructed in various sizes in which the same or similar principles of operation as described above would apply. Furthermore, the figures (and various components shown therein) of the specification are not to be construed as drawn to scale.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Spatially relative terms, such as "front," "rear," "left," "right," "inner," "outer," "beneath", "below", "lower", "above", "upper", "horizontal", "vertical", "lateral", "longitudinal" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Moreover, features described in connection with one embodiment of the invention may be used in conjunction with other embodiments, even if not explicitly stated above. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention.

What is claimed is:

1. A method of designing and evaluating intraocular lenses, comprising:
    generating a first plurality of eye models, wherein each eye model corresponds to a different patient using data that includes constant and customized values, including customized values of a first intraocular lens;
    simulating first peripheral outcomes provided by the first intraocular lens in the first plurality of eye models, wherein the first intraocular lens corresponds to a first patient;
    creating a database of the first outcomes;
    generating a first average for the first peripheral outcomes;
    generating a second plurality of eye models, wherein the first intraocular lens in the first plurality of eye models is substituted with a second intraocular lens which corresponds to a second patient and is different from the first intraocular lens;
    simulating second peripheral outcomes provided by the second intraocular lens in the second plurality of eye models;
    adding the second outcomes to the database;
    generating a second average for the second peripheral outcomes; and
    comparing the first average for the first peripheral outcomes with the second average for the second peripheral outcomes.

2. The method of claim 1, wherein the constant values include at least one of posterior cornea, and retina.

3. The method of claim 1, wherein the customized values further include biometric data and refraction.

4. The method of claim 3, wherein the biometric data includes at least one of anterior cornea, total axial length, and cornea thickness.

5. The method of claim 3, the customized values of the first intraocular lens include at least one of anterior lens geometry, posterior lens geometry, and lens thickness.

6. The method of claim 1, wherein generating the first plurality of eye models includes optimizing anterior chamber depth.

7. The method of claim 1, wherein generating the first plurality of eye models includes validating peripheral outcomes.

8. The method of claim 1, wherein the first plurality of eye models reproduces measured aberrations with an acceptable range of error.

9. The method of claim 8, wherein measured aberrations include at least of defocus, and astigmatism.

10. The method of claim 9, wherein measured aberrations include higher order aberrations.

11. The method of claim 10, wherein the higher order aberrations include at least one of spherical aberrations, horizontal coma, and vertical coma.

12. A system for designing and evaluating intraocular lenses for a large field of view, comprising:
    a plurality of eye models based upon a first intraocular lens, associated with at least one processor, wherein each eye model of said first plurality of eye models corresponds to a different patient and includes a first peripheral aberration average, and wherein the first intraocular lens corresponds to a first patient;
    a simulator provided by the at least one processor that models a second intraocular lens in the plurality of eye models, wherein the second intraocular lens corresponds to a second patient and is different from the first intraocular lens, and wherein the simulator outputs at least one a second peripheral aberration average of the second intraocular lens in the plurality of eye models; and
    a comparator instantiated by the at least one processor that compares differences between the peripheral aberration averages of the first intraocular lens and the second intraocular lens.

* * * * *